(12) United States Patent
Madrid et al.

(10) Patent No.: US 11,408,030 B2
(45) Date of Patent: Aug. 9, 2022

(54) TEST FOR DETECTING ALZHEIMER'S DISEASE

(71) Applicants: Andy Madrid, Madison, WI (US); Reid Spencer Alisch, Prairie du Sac, WI (US); Kirk Jeffrey Hogan, Madison, WI (US)

(72) Inventors: Andy Madrid, Madison, WI (US); Reid Spencer Alisch, Prairie du Sac, WI (US); Kirk Jeffrey Hogan, Madison, WI (US)

(73) Assignees: Andy Madrid, Madison, WI (US); Reid Spencer Alisch, Prairie du Sac, WI (US); Kirk Jeffrey Hogan, Madison, WI (US)

( * ) Notice: Subject to any disclaimer, the term of this patent is extended or adjusted under 35 U.S.C. 154(b) by 166 days.

(21) Appl. No.: 16/564,948

(22) Filed: Sep. 9, 2019

(65) Prior Publication Data

US 2020/0080132 A1   Mar. 12, 2020

Related U.S. Application Data

(60) Provisional application No. 62/729,037, filed on Sep. 10, 2018.

(51) Int. Cl.
*C12Q 1/686* (2018.01)

(52) U.S. Cl.
CPC ........ *C12Q 1/686* (2013.01); *C12Q 2600/154* (2013.01)

(58) Field of Classification Search
CPC .............. C12Q 1/686; C12Q 2600/154
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis et al. |
| 4,965,188 A | 10/1990 | Mullis et al. |
| 5,011,769 A | 4/1991 | Duck et al. |
| 5,124,246 A | 6/1992 | Urdea et al. |
| 5,288,609 A | 2/1994 | Engelhardt et al. |
| 5,338,671 A | 8/1994 | Scalice et al. |
| 5,403,711 A | 4/1995 | Walder et al. |
| 5,409,818 A | 4/1995 | Davey et al. |
| 5,494,810 A | 2/1996 | Barany et al. |
| 5,508,169 A | 4/1996 | Deugau et al. |
| 5,624,802 A | 4/1997 | Urdea et al. |
| 5,639,611 A | 6/1997 | Wallace et al. |
| 5,660,988 A | 8/1997 | Duck et al. |
| 5,710,264 A | 1/1998 | Urdea et al. |
| 5,773,258 A | 6/1998 | Birch et al. |
| 5,786,146 A | 7/1998 | Herman et al. |
| 5,792,614 A | 8/1998 | Western et al. |
| 5,846,717 A | 12/1998 | Brow et al. |
| 5,849,481 A | 12/1998 | Urdea et al. |
| 5,851,770 A | 12/1998 | Babon et al. |
| 5,882,867 A | 3/1999 | Ullman et al. |
| 5,914,230 A | 6/1999 | Liu et al. |
| 5,958,692 A | 9/1999 | Cotton et al. |
| 5,985,557 A | 11/1999 | Prudent et al. |
| 5,994,069 A | 11/1999 | Hall et al. |
| 6,001,567 A | 12/1999 | Brow et al. |
| 6,013,170 A | 1/2000 | Meade et al. |
| 6,063,573 A | 5/2000 | Kayyem |
| 6,090,543 A | 7/2000 | Prudent et al. |
| 6,110,677 A | 8/2000 | Western et al. |
| 6,110,684 A | 8/2000 | Kemper et al. |
| 6,121,001 A | 9/2000 | Western et al. |
| 6,150,097 A | 11/2000 | Tyagi et al. |
| 6,183,960 B1 | 2/2001 | Lizardi et al. |
| 6,210,884 B1 | 4/2001 | Lizardi et al. |
| 6,221,583 B1 | 4/2001 | Kayyem |
| 6,235,502 B1 | 5/2001 | Weissman et al. |
| 6,248,229 B1 | 6/2001 | Meade et al. |
| 6,872,816 B1 | 3/2005 | Hall et al. |
| 7,037,650 B2 | 5/2006 | Gonzalgo et al. |
| 7,662,594 B2 | 2/2010 | Kong et al. |
| 8,361,720 B2 | 1/2013 | Oldham-Haltom et al. |
| 2007/0202525 A1 | 8/2007 | Quake et al. |
| 2009/0253142 A1 | 10/2009 | Allawi et al. |
| 2012/0122088 A1 | 5/2012 | Zou et al. |
| 2012/0122106 A1 | 5/2012 | Zou et al. |

FOREIGN PATENT DOCUMENTS

| | | |
|---|---|---|
| WO | WO200026401 A1 | 5/2000 |
| WO | WO2005023091 A2 | 3/2005 |

OTHER PUBLICATIONS

Du, P. et al., Comparison of Beta-value and M-value methods for quantifying methylation levels by microarray analysis, BMC Bioinf., vol. 11:587, pp. 1-9 (Year: 2010).*
Bock, C. et al., Quantitative comparison of DNA methylation assays for biomarker development and clinical applications, Nature Biotech., vol. 34, pp. 726-737, plus online methods pp. 1-3 (Year: 2016).*
Bakulski, K.M. et al., Genome-Wide DNA Methylation Differences Between Late-Onset Alzheimer's Disease and Cognitively Normal Controls in Human Frontal Cortex, J. Alzheimer's Dis., vol. 29, pp. 571-588 (Year: 2012).*
Bibikova, M. et al., Genome-wide DNA methylation profiling using Infinium assay, Epigenomics, vol. 1, pp. 177-200 (Year: 2009).*
Farré, et al., "Concordant and discordant DNA methylation signatures of aging in human blood and brain", Epigenetics & Chromatin 8, 19 (2015).
Fernández-Pérez, et al., "Role of membrane GM1 on early neuronal membrane actions of Aβ during onset of Alzheimer's disease", Biochimica et Biophysica Acta (BBA)—Molecular Basis of Disease,vol. 1863, Issue 12,2017,pp. 3105-3116.
Fransquet, et al., "Blood DNA methylation as a potential biomarker of dementia: A systematic review", Alzheimer's & Dementia, vol. 14, Issue 1,2018,pp. 81-103.
Johansson, et al, "Prostaglandin signaling suppresses beneficial microglial function in Alzheimer's disease models", J Clin Invest. 2015;125(1): pp. 350-364.

*Primary Examiner* — Teresa E Strzelecka

(74) *Attorney, Agent, or Firm* — Casimir Jones, S.C.; Kirk J. Hogan

(57) ABSTRACT

Provided herein is technology for Alzheimer's disease testing and particularly, but not exclusively, methods, compositions, and related uses for detecting the presence of Alzheimer's disease.

4 Claims, 6 Drawing Sheets

(56) References Cited

OTHER PUBLICATIONS

Johannson, et al., "Inflammatory Cyclooxygenase Activity and $PGE_2$ Signaling in Models of Alzheimer's Disease", Current Immunology Reviews, vol. 11, No. 2, 2015, pp. 125-131(7).
Madrid, et al., "DNA Hypomethylation in Blood Links B3GALT4 and ZADH2 to Alzheimer's Disease", J. Alzheimers Dis, 2018, 66(3), pp. 927-934.
Matsubara, et al., "Size and Shape of Amyloid Fibrils Induced by Ganglioside Nanoclusters: Role of Sialyl Oligosaccharide in Fibril Formation", Langmuir 2017, 33, 48, pp. 13874-13881.
Woodling, et al "Untangling the Web: Toxic and Protective Effects of Neuroinflammation and $PGE_2$ Signaling in Alzheimer's Disease", ACS Chem. Neurosci. 2016, 7, 4, 454-463.
Yanagisawa, "GM1 ganglioside and Alzheimer's Disease", Glycoconj J (2015) 32: pp. 87-91.
Yu, et al., "Methylation profiles in peripheral blood CD4+ lymphocytes versus brain: the relation to Alzheimer's disease pathology", The relation to Alzheimer's disease pathology, Alzheimer's & Dementia, vol. 12, Issue 9, 2016, pp. 942-951.

\* cited by examiner

TEST FOR DETECTING ALZHEIMER'S DISEASE

This work was supported by NIH grants (ADRC P50 AG033514) (S.A.) (R01 AG027161) and NSF grant 1400815. The U.S. government has certain rights in the invention.

FIELD OF INVENTION

Provided herein is technology for Alzheimer's disease testing and particularly, but not exclusively, methods, compositions, and related uses for detecting the presence of Alzheimer's disease.

BACKGROUND

Provided herein is technology for Alzheimer's disease testing and particularly, but not exclusively, methods, compositions, and related uses for detecting the presence of Alzheimer's disease. Covalent addition of a methyl group at position 5 of the nucleotide cytosine generates 5-methylcytosine (5mC) that is most often observed in the human genome adjacent to a guanine in a CpG dinucleotide. Cytosine methylation is less common in dense clusters of CpG dinucleotides referred to as CpG islands that participate in the regulation of gene transcription when located in promoter region (Smith Z D, Meissner A (2013) DNA methylation: roles in mammalian development. *Nat Rev Genet* 14, 204-220.). Fluctuations in 5mC levels across the genome are observed over the lifespan in association with cognitive aging in neurodegeneration, and with changes in learning and memory (Sanchez-Mut J V, Heyn H, Vidal E, Moran S, Sayols S, Delgado-Morales R, Schultz M D, Ansoleaga B, Garcia-Esparcia P, Pons-Espinal M, deLagran M M, Dopazo J, Rabano A, Avila J, Dierssen M, Lott I, Ferrer I, Ecker J R, Esteller M (2016) Human DNA methylomes of neurodegenerative diseases show common epigenomic patterns. *Transl Psychiatry* 6, e718., Day J J, Sweatt J D (2010) DNA methylation and memory formation. *Nat Neurosci* 13, 1319-1323., Day J J, Childs D, Guzman-Karlsson M C, Kibe M, Moulden J, Song E, Tahir A, Sweatt J D (2013) DNA methylation regulates associative reward learning. *Nat Neurosci* 16, 1445-1452.). Variations in 5mC abundance have been identified in postmortem brain tissues of late-onset Alzheimer's disease (LOAD) patients in genes that correlate with LOAD susceptibility. Recent epigenome-wide association studies (EWAS) report differential methylation in known and newly recognized LOAD genes, thereby underscoring the utility of EWAS in disclosing novel genes and pathways associated with LOAD pathogenesis (Bakulski K M, Dolinoy D C, Sartor M A, Paulson H L, Konen J R, Lieberman A P, Albin R L, Hu H, Rozek L S (2012) Genome-wide DNA methylation differences between late-onset Alzheimer's disease and cognitively normal controls in human frontal cortex. *J Alzheimers Dis* 29, 571-588., Lunnon K, Smith R, Hannon E, De Jager P L, Srivastava G, Volta M, Troakes C, Al-Sarraj S, Burrage J, Macdonald R, Condliffe D, Harries L W, Katsel P, Haroutunian V, Kaminsky Z, Joachim C, Powell J, Lovestone S, Bennett D A, Schalkwyk L C, Mill J (2014) Methylomic profiling implicates cortical deregulation of ANK1 in Alzheimer's disease. *Nat Neurosci* 17, 1164-1170, Watson C T, Roussos P, Garg P, Ho D J, Azam N, Katsel P L, Haroutunian V, Sharp A J (2016) Genome-wide DNA methylation profiling in the superior temporal gyms reveals epigenetic signatures associated with Alzheimer's disease. *Genome Med* 8, 5., Coppieters N, Dieriks B V, Lill C, Faull R L, Curtis M A, Dragunow M (2014) Global changes in DNA methylation and hydroxymethylation in Alzheimer's disease human brain. *Neurobiol Aging* 35, 1334-1344.). As an alternative to the study of donor brain tissues, investigation of DNA methylation in accessible peripheral tissues provides an opportunity to improve clinical diagnosis and estimates of prognosis, and to guide personalized treatment of LOAD (Fransquet P D, Lacaze P, Saffery R, McNeil J, Woods R, Ryan J (2018) Blood DNA methylation as a potential biomarker of dementia: A systematic review. *Alzheimers Dement* 14, 81-103.). To identify differences in the distribution of 5mC associated with LOAD, genomic DNA was extracted from the whole blood of 45 LOAD patients and 39 matched controls, and the Illumina HumanMethylationEPIC array was used platform to interrogate >850,000 methylated sites spanning the genome for the presence of differentially methylated positions (DMPs) that distinguish persons with and without LOAD. Results were independently confirmed by pyrosequencing targeted loci.

SUMMARY

In some embodiments, the present invention provides methods, compositions, systems and kits for measuring the methylation level of one or more differentially methylated positions (DMPs) in B3GALT4 and/or ZADH2 comprising: a) extracting genomic DNA from a blood sample of a human individual suspected of having or having Alzheimer's disease; b) treating the extracted genomic DNA with bisulfite; c) amplifying the bisulfite-treated genomic DNA with primers comprising a pair of primers specific for B3GALT4 and a pair of primers specific for ZADH2; and d) measuring the methylation level of one or more differentially methylated positions (DMPs) in B3GALT4 and/or ZADH2 by methylation-specific PCR, quantitative methylation-specific PCR, methylation sensitive DNA restriction enzyme analysis, methylation sensitive microarray analysis, methylation-sensitive pyrosequencing, bisulfite genomic sequencing PCR, or whole methylome sequencing.

In some embodiments, the present invention provides a method of detecting Alzheimer's disease in a patient, comprising obtaining a sample from said patient, and determining the methylation status of at least one CpG locus in a defined subset of CpG loci in B3GALT4, ZADH2 and/or other differentially methylated Alzheimer's disease marker nucleic acid molecules, wherein methylation at each of said CpG loci in said defined set of CpG loci in said Alzheimer's disease marker nucleic acid is indicative of Alzheimer's disease in said patient. In certain embodiments, the defined subset of CpG loci comprises at least three CpG loci. In other embodiments, the determining comprises analysis of the CpG loci in a nucleic acid detection assay configured to determine the methylation status of each of said loci in a single nucleic acid detection assay, wherein the assay is a primer extension assay, a nucleic acid amplification assay, a nucleic acid sequencing assay, a structure specific cleavage assay, a 5'nuclease cleavage assay, an invasive cleavage assay or a ligation assay. In further embodiments, the determining comprises treating DNA from the sample with a bisulfite reagent, In still further embodiments, the subset of differentially methylated Alzheimer's disease marker nucleic acid molecules comprises nucleic acid molecules form a plurality of Alzheimer's disease marker nucleic acid molecules. In particular embodiments, the plurality of Alzheimer's disease marker nucleic acid molecules comprises at least three Alzheimer's disease marker nucleic acid molecules.

In some embodiments, the present invention provides methods for treating a patient with an anti-Alzheimer's disease agent wherein the patient is suffering from Alzheimer's disease, the method comprising the steps of determining or having determined the presence of differential methylation of one or more CpG loci in B3GALT4 and/or ZADH2 in a sample by extracting genomic DNA from a blood sample of a human individual suspected of having or having Alzheimer's disease, treating the extracted genomic DNA with bisulfate, amplifying the bisulfite-treated genomic DNA with primers comprising a pair of primers specific for B3GALT4 and a pair of primers specific for ZADH2, and measuring the methylation level of one or more differentially methylated positions (DMPs) in B3GALT4 and/or ZADH2 by methylation-specific PCR, quantitative methylation-specific PCR, methylation sensitive DNA restriction enzyme analysis, methylation sensitive microarray analysis, methylation-sensitive pyrosequencing, bisulfite genomic sequencing PCR or whole methylome sequencing, and treating the patient with an anti-Alzheimer's disease agent if differential methylation of one or more CpG loci in B3GALT4 and/or ZADH2 is present.

DESCRIPTION OF THE DRAWINGS

FIG. 1 shows differentially methylated positions (DMPs) in white blood cell DNA between LOAD patients and matched no-LOAD persons. The Venn diagram depicts differentially methylated CpG sites within each of 7 comparison groups (LOAD vs. non-LOAD, Rey Auditory Verbal Learning Test (RAVLT) scores, h-tau, and p-tau$_{181}$ levels, and t-tau/Abeta$_{42}$, p-tau/Abeta$_{42}$, and Abeta$_{42}$/Abeta$_{40}$ ratios. Numerical values within each oval are the number of DMPs identified for each variable. Seventeen DMPs were shared between all comparisons.

FIGS. 2A-2B show relative positions of LOAD vs. no-LOAD differentially methylated positions (DMPs) at B3GALT4 and ZADH2 loci. FIG. 2A (Upper panel) Schematic of B3GALT4 and its neighboring gene RSP18. The relative positions of probes measuring methylation levels of CpG sites annotated to B3GALT4 with their genomic 5'-3' positions are provided (inset panel; x-axis) vs. the $-\log_{10}$ of the adjusted local index of significant (aLIS) P-value (y-axis). All probes were tested for hypermethylation (triangles) and hypomethylation (dots). Levels of aLIS P-values <0.05 (dashed line) and <0.01 (continuous line) are displayed. In the LOAD vs. no-LOAD comparison, 13 hypomethylated probes (n=13 exonic probes) exhibit an aLIS P-value <0.05. Their relative locations are highlighted by a bracket and an asterisk. The CpG IDs of the 12 probes with DMPs in B3GALT4 in all 7 comparisons are: cg03127244, cg22878489, cg03721978, cg09349343, cg17103217, cg23950233, cg21618521, cg19882268, cg00052772, cg27147350, cg06362282, cg24605046. The LOAD vs. no-LOAD CpG DMP site cg26055446 was not shared between the 7 comparisons (hollow dot). FIG. 2B (Lower panel) Schematic of ZADH2 and its neighboring gene TSHZ1. The relative positions of probes measuring methylation levels of CpG sites annotated to ZADH2 with their genomic 5'-3' positions are provided (inset panel; x-axis) vs. the $-\log_{10}$ of the aLIS P-value (y-axis). All probes were tested for hypermethylation (triangles) and hypomethylation (dots). Levels of aLIS P-values <0.05 (dashed line) and <0.01 (continuous line) are displayed. In the LOAD vs. no-LOAD comparison, 8 hypomethylated probes (n=5 intronic, n=3 exonic) exhibit an aLIS P-value <0.05. Their relative locations are highlighted by a bracket and an asterisk. The CpG IDs of the 5 probes with DMPs in ZADH2 in all 7 comparisons are: cg02750262, cg18449964, cg03972071, cg07889413, cg22088248. The LOAD vs. no-LOAD CpG DMP sites cg21786191, cg21330207 and cg11568697 were not shared between the 7 comparisons (hollow dots).

FIG. 3 shows pyrosequencing probe sets for 7 B3GALT4 DMPs used to confirm the validity of the findings of the 850K array data. The mean correlation between DNA methylation at these DMPs using the HumanMethylation-EPIC microarray and pyrosequencing is >0.9, thereby providing evidence of a high level of convergence between the two methylation platforms in analysis of samples from patients with LOAD and participants without LOAD.

FIG. 4 shows pyrosequencing probe sets for 5 ZADH2 DMPs used to confirm the validity of the findings of the 850K array data. The mean correlation between DNA methylation at these DMPs using the HumanMethylation-EPIC microarray and pyrosequencing is >0.9, thereby providing evidence of a high level of convergence between the two methylation platforms in analysis of samples from patients with LOAD and participants without LOAD.

DEFINITIONS

Figure 1:
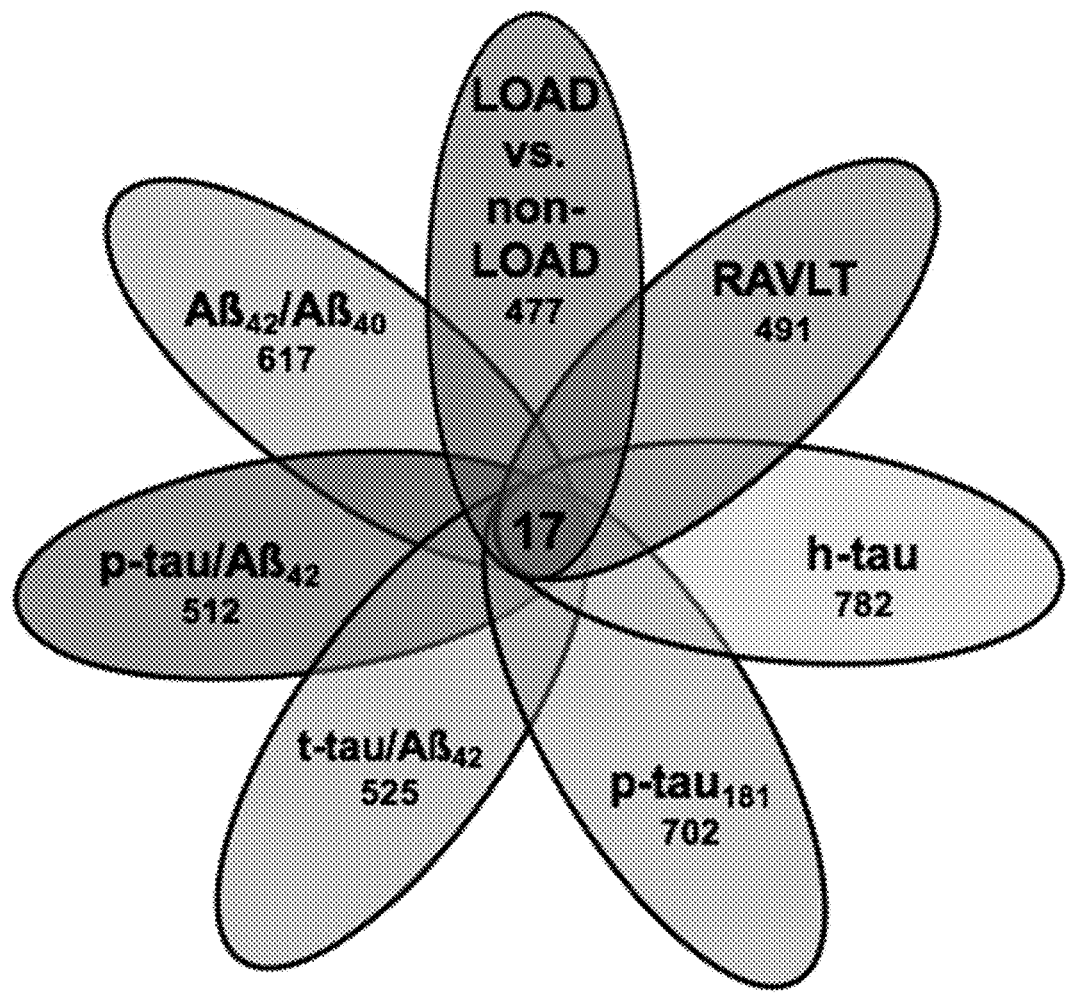
FIG. 1.

To facilitate an understanding of the present technology, a number of terms and phrases are defined below. Additional definitions are set forth throughout the detailed description. Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, a "nucleic acid" or "nucleic acid molecule" generally refers to any ribonucleic acid or deoxyribonucleic acid, which may be unmodified or modified DNA or RNA. "Nucleic acids" include, without limitation, single- and double-stranded nucleic acids. As used herein, the term "nucleic acid" also includes DNA as described above that contains one or more modified bases. Thus, DNA with a backbone modified for stability or for other reasons is a "nucleic acid". The term "nucleic acid" as it is used herein embraces such chemically, enzymatically, or metabolically modified forms of nucleic acids, as well as the chemical forms of DNA characteristic of viruses and cells, including for example, simple and complex cells.

The terms "oligonucleotide" or "polynucleotide" or "nucleotide" or "nucleic acid" refer to a molecule having two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. Typical deoxyribonucleotides for DNA are thymine, adenine, cytosine, and guanine. Typical ribonucleotides for RNA are uracil, adenine, cytosine, and guanine.

As used herein, the terms "locus" or "region" of a nucleic acid refer to a sub-region of a nucleic acid, e.g., a gene on a chromosome, a single nucleotide, a CpG island, etc.

The terms "complementary" and "complementarity" refer to nucleotides (e.g., 1 nucleotide) or polynucleotides (e.g., a sequence of nucleotides) related by the base-pairing rules. For example, the sequence 5'-A-G-T-3' is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands effects the efficiency and strength of hybridization between nucleic acid strands. This is of particular importance in amplification reactions and in detection methods that depend upon binding between nucleic acids.

The term "gene" refers to a nucleic acid (e.g., DNA or RNA) sequence that comprises coding sequences necessary for the production of an RNA, or of a polypeptide or its precursor. A functional polypeptide can be encoded by a full-length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends, e.g., for a distance of about 1 kb on either end, such that the gene corresponds to the length of the full-length mRNA (e.g., comprising coding, regulatory, structural and other sequences). The sequences that are located 5' of the coding region and that are present on the mRNA are referred to as 5' non-translated or untranslated sequences. The sequences that are located 3' or downstream of the coding region and that are present on the mRNA are referred to as 3' non-translated or 3' untranslated sequences. The term "gene" encompasses both cDNA and genomic forms of a gene. In some organisms (e.g., eukaryotes), a genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' ends of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage, and polyadenylation.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by the hand of a person in the laboratory is naturally-occurring. A wild-type gene is often that gene or allele that is most frequently observed in a population and is thus arbitrarily designated the "normal" or "wild-type" form of the gene. In contrast, the term "modified" or "mutant" when made in reference to a gene or to a gene product refers, respectively, to a gene or to a gene product that displays modifications in sequence and/or functional properties (e.g., altered characteristics) when compared to the wild-type gene or gene product. It is noted that naturally-occurring mutants can be isolated; these are identified by the fact that they have altered characteristics when compared to the wild-type gene or gene product.

The term "allele" refers to a variation of a gene; the variations include but are not limited to variants and mutants, polymorphic loci, and single nucleotide polymorphic loci, frameshift, and splice mutations. An allele may occur naturally in a population or it might arise during the lifetime of any particular individual of the population.

Thus, the terms "variant" and "mutant" when used in reference to a nucleotide sequence refer to a nucleic acid sequence that differs by one or more nucleotides from another, usually related, nucleotide acid sequence. A "variation" is a difference between two different nucleotide sequences; typically, one sequence is a reference sequence.

"Amplification" is a special case of nucleic acid replication involving template specificity. It is to be contrasted with non-specific template replication (e.g., replication that is template-dependent but not dependent on a specific template). Template specificity is here distinguished from fidelity of replication (e.g., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Amplification of nucleic acids generally refers to the production of multiple copies of a polynucleotide, or a portion of the polynucleotide, typically starting from a small amount of the polynucleotide (e.g., a single polynucleotide molecule, 10 to 100 copies of a polynucleotide molecule, which may or may not be exactly the same), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810) are forms of amplification. Additional types of amplification include, but are not limited to, allele-specific PCR (see, e.g., U.S. Pat. No. 5,639,611), assembly PCR (see, e.g., U.S. Pat. No. 5,965,408), helicase-dependent amplification (see, e.g., U.S. Pat. No. 7,662,594), Hot-start PCR (see, e.g., U.S. Pat. Nos. 5,773,258 and 5,338,671), intersequence-specific PCR, inverse PCR (see, e.g., Triglia, et al. (1988) Nucleic Acids Res., 16:8186), ligation-mediated PCR (see, e.g., Guilfoyle, R. et al., Nucleic Acids Research, 25:1854-1858 (1997); U.S. Pat. No. 5,508,169), methylation-specific PCR (see, e.g., Herman, et al., (1996) PNAS 93(13) 9821-9826), miniprimer PCR, multiplex ligation-dependent probe amplification (see, e.g., Schouten, et al., (2002) Nucleic Acids Research 30(12): e57), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80), nested PCR, overlap-extension PCR (see, e.g., Higuchi, et al., (1988) Nucleic Acids Research 16(15) 7351-7367), real time PCR (see, e.g., Higuchi, et al., (1992) Biotechnology 10:413-417; Higuchi, et al., (1993) Biotechnology 11:1026-1030), reverse transcription PCR (see, e.g., Bustin, S. A. (2000) J. Molecular Endocrinology 25:169-193), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is de-natured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons."

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q-beta replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlin et al, Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics 4:560). Finally, thermostable template-dependent DNA polymerases (e.g., Taq and Pfu DNA polymerases), by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, Hologic, Inc.) and are described, e.g., in U.S. Pat. Nos. 5,846,717, 5,985, 557, 5,994,069, 6,001,567, 6,090,543, and 6,872,816; Lyamichev et al., Nat. Biotech., 17:292 (1999), Hall et al., PNAS, USA, 97:8272 (2000), and US 2009/0253142); enzyme mismatch cleavage methods (e.g., Variagenics, U.S. Pat. Nos. 6,110,684, 5,958,692, 5,851,770); polymerase chain reaction; branched hybridization methods (e.g., Chiron, U.S. Pat. Nos. 5,849,481, 5,710,264, 5,124,246, and 5,624,802); rolling circle replication (e.g., U.S. Pat. Nos. 6,210,884, 6,183,960 and 6,235,502); NASBA (e.g., U.S. Pat. No. 5,409,818); molecular beacon technology (e.g., U.S. Pat. No. 6,150,097); E-sensor technology (Motorola, U.S. Pat. Nos. 6,248,229, 6,221,583, 6,013,170, and 6,063, 573); cycling probe technology (e.g., U.S. Pat. Nos. 5,403, 711, 5,011,769, and 5,660,988); Dade Behring signal amplification methods (e.g., U.S. Pat. Nos. 6,121,001, 6,110,677, 5,914,230, 5,882,867, and 5,792,614); ligase chain reaction (e.g., Barnay, Proc. Natl. Acad. Sci USA 88, 189-93 (1991)); and sandwich hybridization methods (e.g., U.S. Pat. No. 5,288,609).

The term "amplifiable nucleic acid" refers to a nucleic acid that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as a DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, "methylation" refers to cytosine methylation at positions C5 or N4 of cytosine, the N6 position of adenine, or other types of nucleic acid methylation. In vitro amplified DNA is usually unmethylated because typical in vitro DNA amplification methods do not retain the methylation pattern of the amplification template. However, "unmethylated DNA" or "methylated DNA" can also refer to amplified DNA whose original template was unmethylated or methylated, respectively.

Accordingly, as used herein a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring; however, for purposes herein, thymine is not considered a methylated nucleotide when present in DNA since thymine is a typical nucleotide base of DNA.

As used herein, a "methylated nucleic acid molecule" refers to a nucleic acid molecule that contains one or more methylated nucleotides.

As used herein, a "methylation state", "methylation profile", and "methylation status" of a nucleic acid molecule refers to the presence of absence of one or more methylated nucleotide bases in the nucleic acid molecule. For example, a nucleic acid molecule containing a methylated cytosine is considered methylated (e.g., the methylation state of the nucleic acid molecule is methylated). A nucleic acid molecule that does not contain any methylated nucleotides is considered unmethylated.

The methylation state of a particular nucleic acid sequence (e.g., a gene marker or DNA region as described herein) can indicate the methylation state of every base in the sequence or can indicate the methylation state of a subset of the bases (., of one or more cytosines) within the sequence, or can indicate information regarding regional methylation density within the sequence with or without providing precise information of the locations within the sequence the methylation occurs.

The methylation state of a nucleotide locus in a nucleic acid molecule refers to the presence or absence of a methylated nucleotide at a particular locus in the nucleic acid molecule. For example, the methylation state of a cytosine at the 7th nucleotide in a nucleic acid molecule is methylated when the nucleotide present at the 7th nucleotide in the nucleic acid molecule is 5-methylcytosine. Similarly, the methylation state of a cytosine at the 7th nucleotide in a nucleic acid molecule is unmethylated when the nucleotide present at the 7th nucleotide in the nucleic acid molecule is cytosine (and not 5-methylcytosine).

The methylation status can optionally be represented or indicated by a "methylation value" (e.g., representing a methylation frequency, fraction, ratio, percent, etc.) A methylation value can be generated, for example, by quantifying the amount of intact nucleic acid present following restriction digestion with a methylation dependent restriction enzyme or by comparing amplification profiles after bisulfite reaction or by comparing sequences of bisulfite-treated and untreated nucleic acids. Accordingly, a value, e.g., a methylation value, represents the methylation status and can thus be used as a quantitative indicator of methylation status across multiple copies of a locus. This is of particular use when it is desirable to compare the methylation status of a sequence in a sample to a threshold or reference value.

As used herein, "methylation frequency" or "methylation percent (%)" refer to the number of instances in which a molecule or locus is methylated relative to the number of instances the molecule or locus is unmethylated.

As such, the methylation state describes the state of methylation of a nucleic acid (e.g., a genomic sequence). In addition, the methylation state refers to the characteristics of a nucleic acid segment at a particular genomic locus relevant to methylation. Such characteristics include, but are not limited to, whether any of the cytosine (C) residues within this DNA sequence are methylated, the location of methylated C residue(s), the frequency or percentage of methylated C throughout any particular region of a nucleic acid, and allelic differences in methylation due to, e.g., difference in the origin of the alleles. The terms "methylation state", "methylation profile", and "methylation status" also refer to the relative concentration, absolute concentration, or pattern of methylated C or unmethylated C throughout any particular region of a nucleic acid in a biological sample. For example, if the cytosine (C) residue(s) within a nucleic acid sequence are methylated it may be referred to as "hypermethylated" or having "increased methylation", whereas if the cytosine (C) residue(s) within a DNA sequence are not methylated it may be referred to as "hypomethylated" or having "decreased methylation". Likewise, if the cytosine (C) residue(s) within a nucleic acid sequence are methylated as compared to another nucleic acid sequence (e.g., from a different region or from a different individual, etc.) that sequence is considered hypermethylated or having increased methylation compared to the other nucleic acid sequence. Alternatively, if the cytosine (C) residue(s) within a DNA sequence are not methylated as compared to another nucleic acid sequence (e.g., from a different region or from a different individual, etc.) that sequence is considered hypomethylated or having decreased methylation compared to the other nucleic acid sequence. Additionally, the term "methylation pattern" as used herein refers to the collective sites of methylated and unmethylated nucleotides over a region of a nucleic acid. Two nucleic acids may have the same or similar methylation frequency or methylation percent but have different methylation patterns when the number of methylated and unmethylated nucleotides are the same or similar throughout the region but the locations of methylated and unmethylated nucleotides are different. Sequences are said to be "differentially methylated" or as having a "difference in methylation" or having a "different methylation state" when they differ in the extent (e.g., one has increased or decreased methylation relative to the other), frequency, or pattern of methylation. The term "differential methylation" refers to a difference in the level or pattern of nucleic acid methylation in an Alzheimer's disease positive sample as compared with the level or pattern of nucleic acid methylation in a Alzheimer's disease negative sample. Differential methylation and specific levels or patterns of DNA methylation are prognostic and predictive biomarkers, e.g., once the correct cut-off or predictive characteristics have been defined.

Methylation state frequency can be used to describe a population of individuals or a sample from a single individual. For example, a nucleotide locus having a methylation state frequency of 50% is methylated in 50% of instances and unmethylated in 50% of instances. Such a frequency can be used, for example, to describe the degree to which a nucleotide locus or nucleic acid region is methylated in a population of individuals or a collection of nucleic acids. Thus, when methylation in a first population or pool of nucleic acid molecules is different from methylation in a second population or pool of nucleic acid molecules, the methylation state frequency of the first population or pool will be different from the methylation state frequency of the second population or pool. Such a frequency also can be used, for example, to describe the degree to which a nucleotide locus or nucleic acid region is methylated in a single individual. For example, such a frequency can be used to describe the degree to which a group of cells from a tissue sample are methylated or unmethylated at a nucleotide locus or nucleic acid region.

As used herein a "nucleotide locus" refers to the location of a nucleotide in a nucleic acid molecule. A nucleotide locus of a methylated nucleotide refers to the location of a methylated nucleotide in a nucleic acid molecule.

Typically, methylation of human DNA occurs on a dinucleotide sequence including an adjacent guanine and cytosine where the cytosine is located 5' of the guanine (also termed CpG dinucleotide sequences). Most cytosines within the CpG dinucleotides are methylated in the human genome, however some remain unmethylated in specific CpG dinucleotide rich genomic regions, known as CpG islands (see, e.g, Antequera et al. (1990) *Cell* 62: 503-514).

As used herein, a "CpG island" refers to a G:C-rich region of genomic DNA containing an increased number of CpG dinucleotides relative to total genomic DNA. A CpG island can be at least 100, 200, or more base pairs in length, where the G:C content of the region is at least 50% and the ratio of observed CpG frequency over expected frequency is 0.6; in some instances, a CpG island can be at least 500 base pairs in length, where the G:C content of the region is at least 55%) and the ratio of observed CpG frequency over expected frequency is 0.65. The observed CpG frequency over expected frequency can be calculated according to the method provided in Gardiner-Garden et al. (1987) *J. Mol. Biol.* 196: 261-281. For example, the observed CpG frequency over expected frequency can be calculated according to the formula $R=(A \times B)/(C \times D)$, where R is the ratio of observed CpG frequency over expected frequency, A is the number of CpG dinucleotides in an analyzed sequence, B is the total number of nucleotides in the analyzed sequence, C is the total number of C nucleotides in the analyzed sequence, and D is the total number of G nucleotides in the analyzed sequence. Methylation state is typically determined in CpG islands, e.g., at promoter regions. It will be appreciated though that other sequences in the human genome are prone to DNA methylation such as CpA and CpT (see, e.g., Ramsahoye (2000) Proc. Natl. Acad. Sci. USA 97: 5237-5242; Salmon and Kaye (1970) Biochim. Biophys. Acta. 204: 340-351; Grafstrom (1985) Nucleic Acids Res. 13: 2827-2842; Nyce (1986) Nucleic Acids Res. 14: 4353-4367; Woodcock (1987) Biochem. Biophys. Res. Commun. 145: 888-894).

As used herein, a reagent that modifies a nucleotide of the nucleic acid molecule as a function of the methylation state of the nucleic acid molecule, or a methylation-specific reagent, refers to a compound or composition or other agent that can change the nucleotide sequence of a nucleic acid molecule in a manner that reflects the methylation state of the nucleic acid molecule. Methods of treating a nucleic acid molecule with such a reagent can include contacting the nucleic acid molecule with the reagent, coupled with additional steps, if desired, to accomplish the desired change of nucleotide sequence. Such a change in the nucleic acid molecule's nucleotide sequence can result in a nucleic acid molecule in which each methylated nucleotide is modified to a different nucleotide. Such a change in the nucleic acid nucleotide sequence can result in a nucleic acid molecule in which each unmethylated nucleotide is modified to a different nucleotide. Such a change in the nucleic acid nucleotide sequence can result in a nucleic acid molecule in which each of a selected nucleotide which is unmethylated (e.g., each unmethylated cytosine) is modified to a different nucleotide. Use of such a reagent to change the nucleic acid nucleotide sequence can result in a nucleic acid molecule in which each nucleotide that is a methylated nucleotide (e.g., each methylated cytosine) is modified to a different nucleotide. As used herein, use of a reagent that modifies a selected nucleotide refers to a reagent that modifies one nucleotide of the four typically occurring nucleotides in a nucleic acid molecule (C, G, T, and A for DNA and C, G, U, and A for RNA), such that the reagent modifies the one nucleotide without modifying the other three nucleotides. In one exemplary embodiment, such a reagent modifies an unmethylated selected nucleotide to produce a different nucleotide. In another exemplary embodiment, such a reagent can deaminate unmethylated cytosine nucleotides. An exemplary reagent is bisulfite.

As used herein, the term "bisulfite reagent" refers to a reagent comprising in some embodiments bisulfite, disulfite, hydrogen sulfite, or combinations thereof to distinguish between methylated and unmethylated cytidines, e.g., in CpG dinucleotide sequences.

The term "methylation assay" refers to any assay for determining the methylation state of one or more CpG dinucleotide sequences within a sequence of a nucleic acid.

The term "MS AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al. (1997) Cancer Research 57: 594-599.

The term "METHYLIGHT™" refers to the art-recognized fluorescence-based real-time PCR technique described by Eads et al. (1999) Cancer Res. 59: 2302-2306.

The term "HEAVYMETHYL™" refers to an assay wherein methylation specific blocking probes (also referred to herein as blockers) covering CpG positions between, or covered by, the amplification primers enable methylation-specific selective amplification of a nucleic acid sample.

The term "HEAVYMETHYL™ METHYLIGHT™" assay refers to a HEAVYMETHYL™ METHYLIGHT™ assay, which is a variation of the METHYLIGHT™ assay, wherein the METHYLIGHT™ assay is combined with methylation specific blocking probes covering CpG positions between the amplification primers.

The term "MS-SNUPE" (Methylation-sensitive Single Nucleotide Primer Extension) refers to the art-recognized assay described by Gonzalgo & Jones (1997) Nucleic Acids Res. 25: 2529-2531.

The term "MSP" (Methylation-specific PCR) refers to the art-recognized methylation assay described by Herman et al. (1996) Proc. Natl. Acad. Sci. USA 93: 9821-9826, and by U.S. Pat. No. 5,786,146.

The term "COBRA" (Combined Bisulfite Restriction Analysis) refers to the art-recognized methylation assay described by Xiong & Laird (1997) Nucleic Acids Res. 25: 2532-2534.

The term "MCA" (Methylated CpG Island Amplification) refers to the methylation assay described by Toyota et al. (1999) Cancer Res. 59: 2307-12, and in WO 00/26401A1.

As used herein, a "selected nucleotide" refers to one nucleotide of the four typically occurring nucleotides in a nucleic acid molecule (C, G, T, and A for DNA and C, G, U, and A for RNA), and can include methylated derivatives of the typically occurring nucleotides (e.g., when C is the selected nucleotide, both methylated and unmethylated C are included within the meaning of a selected nucleotide), whereas a methylated selected nucleotide refers specifically to a methylated typically occurring nucleotide and an unmethylated selected nucleotides refers specifically to an unmethylated typically occurring nucleotide.

The terms "methylation-specific restriction enzyme" or "methylation-sensitive restriction enzyme" refers to an enzyme that selectively digests a nucleic acid dependent on the methylation state of its recognition site. In the case of a restriction enzyme that specifically cuts if the recognition site is not methylated or is hemi-methylated, the cut will not take place or will take place with a significantly reduced efficiency if the recognition site is methylated. In the case of a restriction enzyme that specifically cuts if the recognition site is methylated, the cut will not take place or will take place with a significantly reduced efficiency if the recognition site is not methylated. Preferred are methylation-specific restriction enzymes, the recognition sequence of which contains a CG dinucleotide (for instance a recognition sequence such as CGCG or CCCGGG). Further preferred for some embodiments are restriction enzymes that do not cut if the cytosine in this dinucleotide is methylated at the carbon atom C5.

As used herein, a "different nucleotide" refers to a nucleotide that is chemically different from a selected nucleotide, typically such that the different nucleotide has Watson-Crick base-pairing properties that differ from the selected nucleotide, whereby the typically occurring nucleotide that is complementary to the selected nucleotide is not the same as the typically occurring nucleotide that is complementary to the different nucleotide. For example, when C is the selected nucleotide, U or T can be the different nucleotide, which is exemplified by the complementarity of C to G and the complementarity of U or T to A. As used herein, a nucleotide that is complementary to the selected nucleotide or that is complementary to the different nucleotide refers to a nucleotide that base-pairs, under high stringency conditions, with the selected nucleotide or different nucleotide with higher affinity than the complementary nucleotide's base-paring with three of the four typically occurring nucleotides. An example of complementarity is Watson-Crick base pairing in DNA (e.g., A-T and C-G) and RNA (e.g., A-U and C-G). Thus, for example, G base-pairs, under high stringency conditions, with higher affinity to C than G base-pairs to G, A, or T and, therefore, when C is the selected nucleotide, G is a nucleotide complementary to the selected nucleotide.

As used herein, the "sensitivity" of a given marker refers to the percentage of samples that report a DNA methylation value above a threshold value that distinguishes between Alzheimer's disease and non-Alzheimer's disease samples. The value of sensitivity, therefore, reflects the probability that a DNA methylation measurement for a given marker obtained from a known diseased sample will be in the range of disease-associated measurements. As defined here, the clinical relevance of the calculated sensitivity value represents an estimation of the probability that a given marker would detect the presence of a clinical condition when applied to a subject with that condition.

As used herein, the "specificity" of a given marker refers to the percentage of non-Alzheimer's disease samples that report a DNA methylation value below a threshold value that distinguishes between Alzheimer's disease and non-Alzheimer's disease samples. The value of specificity, therefore, reflects the probability that a DNA methylation measurement for a given marker obtained from a known non-Alzheimer's disease sample will be in the range of non-disease associated measurements. As defined here, the clinical relevance of the calculated specificity value represents an estimation of the probability that a given marker would detect the absence of a clinical condition when applied to a patient without that condition.

The term "AUC" as used herein is an abbreviation for the "area under a curve". In particular it refers to the area under a Receiver Operating Characteristic (ROC) curve. The ROC curve is a plot of the true positive rate against the false positive rate for the different possible cut points of a diagnostic test. It shows the trade-off between sensitivity and specificity depending on the selected cut point (any increase in sensitivity will be accompanied by a decrease in specificity). The area under an ROC curve (AUC) is a measure for the accuracy of a diagnostic test (the larger the area the better; the optimum is 1; a random test would have a ROC curve lying on the diagonal with an area of 0.5; for reference: J. P. Egan. (1975) Signal Detection Theory and ROC Analysis, Academic Press, New York).

As used herein, a "diagnostic" test application includes the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition. For example, a diagnostic can be used for detecting the presence or likelihood of a subject contracting Alzheimer's disease, or the likelihood that such a subject will respond favorably to a compound (e.g., a pharmaceutical, e.g., a drug) or other treatment.

The term "marker", as used herein, refers to a substance (e.g., a nucleic acid or a region of a nucleic acid) that is able to diagnose Alzheimer's disease by distinguishing abnormal cells from normal cells, e.g., based its methylation state.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may be single-stranded), but may contain both the sense and anti-sense strands (i.e., the oligonucleotide may be double-stranded). An isolated nucleic acid may, after isolation from its natural or typical environment, by be combined with other nucleic acids or molecules. For example, an isolated nucleic acid may be present in a host cell in which into which it has been placed, e.g., for heterologous expression.

The term "purified" refers to molecules, either nucleic acid or amino acid sequences that are removed from their natural environment, isolated, or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the terms "purified" or "to purify" also refer to the removal of contaminants from a sample. The removal of contaminating proteins results in an increase in the percent of polypeptide or nucleic acid of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution containing salts (e.g., NaCl), detergents (e.g., SDS), and other components (e.g., Denhardt's solution, dry milk, salmon sperm DNA, etc.).

The term "sample" is used in its broadest sense. In one sense it can refer to an animal cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

As used herein, the terms "patient" or "subject" refer to organisms to be subject to various tests provided by the technology. The term "subject" includes animals, preferably mammals, including humans. In a one embodiment, the subject is a primate. In another embodiment, the subject is a human.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a sub-portion of the total kit components. The containers may be delivered to the intended recipient together or separately. For example, a first container may contain an enzyme for use in an assay, while a second container contains oligonucleotides. The term "fragmented kit" is intended to encompass kits containing Analyte Specific Reagents (ASR's) regulated under section 520(e) of the Federal Food, Drug, and Cosmetic Act, but are not limited thereto. Indeed, any delivery system comprising two or more separate containers that each contains a sub-portion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

DETAILED DESCRIPTION AND EXAMPLES

Differentially methylated positions (DMPs) between persons with and without late-onset Alzheimer's disease (LOAD) were observed at 477 of 769,190 loci in a plurality of genes. Of these, 17 were shared with DMPs identified using clinical LOAD markers analyzed independently as continuous variables comprising Rey Auditory Verbal Learning Test (RAVLT) scores, cerebrospinal fluid total tau (t-tau) and phosphorylated tau 181 (p-tau$_{181}$) levels, and t-tau/Abeta1-42 (Abeta$_{42}$), p-tau$_{181}$/Abeta$_{42}$, and Abeta$_{42}$/Abeta1-40 (Abeta$_{40}$) ratios. In patients with LOAD, 12 of the shared 17 DMPs were hypomethylated in B3GALT4 (Beta-1,3-galatcosyltransferase 4) (EC 2.4.1.62), and 5 were hypomethylated in ZADH2 (Prostaglandin reductase 3) (EC 1.3.1.48).

Materials and Methods

Participants

Participants were 45 patients with a clinical diagnosis of LOAD based on NIA-AA criteria, and 39 persons without cognitive impairment matched for age, sex and education who are enrolled in the longitudinal Wisconsin Alzheimer's Disease Research Center (WADRC) clinical core. Participants in the WADRC clinical core are evaluated annually with a panel of cognitive performance tests. Cognitive status is determined by a consensus conference panel based on National Institute on Aging-Alzheimer's Association criteria (Albert M S, DeKosky S T, Dickson D, Dubois B, Feldman H H, Fox N C, Gamst A, Holtzman D M, Jagust W J, Petersen R C, Snyder P J, Carrillo M C, Thies B, Phelps C H (2011) The diagnosis of mild cognitive impairment due to Alzheimer's disease: recommendations from the National Institute on Aging-Alzheimer's Association workgroups on diagnostic guidelines for Alzheimer's disease. *Alzheimers Dement* 7, 270-279., McKhann G M, Knopman D S, Chertkow H, Hyman B T, Jack C R, Jr., Kawas C H, Klunk W E, Koroshetz W J, Manly J J, Mayeux R, Mohs R C, Morris J C, Rossor M N, Scheltens P, Carrillo M C, Thies B, Weintraub S, Phelps C H (2011) The diagnosis of dementia due to Alzheimer's disease: recommendations from the National Institute on Aging-Alzheimer's Association workgroups on diagnostic guidelines for Alzheimer's disease. *Alzheimers Dement* 7, 263-269.).

Neuropsychological Assessment

Measures of learning and memory (Rey Auditory Verbal Learning Test (RAVLT), Total Trials and Delayed Recall), and executive function (Trail Making Test Part B (TMT-B)) were included based on prior meta-analyses indicating that these cognitive domains demonstrate significant decline and association with LOAD biomarkers (Reitan R M (1994) Ward Halstead's contributions to neuropsychology and the Halstead-Reitan Neuropsychological Test Battery. *J Clin Psychol* 50, 47-70, Backman L, Jones S, Berger A K, Laukka E J, Small B J (2005) Cognitive impairment in preclinical Alzheimer's disease: a meta-analysis. *Neuropsychology* 19, 520-531, Hedden T, Oh H, Younger A P, Patel T A (2013) Meta-analysis of amyloid-cognition relations in cognitively normal older adults. *Neurology* 80, 1341-1348., Duke Han S, Nguyen C P, Stricker N H, Nation D A (2017) Detectable Neuropsychological Differences in Early Preclinical Alzheimer's Disease: A Meta-Analysis. *Neuropsychol Rev* 27, 305-325., Schmidt M (1996) in *Western Psychological Services*, Los Angeles.).

Cerebrospinal Fluid (CSF) Amyloid and Tau

CSF was collected in the morning after a minimum 12-hour fast, as previously described (Clark L R, Berman S E, Norton D, Koscik R L, Jonaitis E, Blennow K, Bendlin B B, Asthana S, Johnson S C, Zetterberg H, Carlsson C M (2018) Age-accelerated cognitive decline in asymptomatic adults with CSF beta-amyloid. Neurology 90, e1306-e1315.). Samples were sent to the Clinical Neurochemistry Laboratory at the Sahlgrenska Academy of the University of Gothenburg, Sweden, and analyzed according to protocols approved by the Swedish Board of Accreditation and Conformity Assessment using one batch of reagents (intra-assay coefficients of variation <10%) for each of two batches. CSF samples were assayed for total tau (t-tau), phosphorylated tau 181 (p-tau$_{181}$), Abeta1-42 (Abeta$_{42}$), and Abeta1-40 (Abeta$_{40}$) using commercially available ELISA methods (INNOTEST assays, Fujirebio, Ghent, Belgium), and (Abeta$_{42}$/Abeta$_{40}$) ratios (Triplex assays, MSD Human Abeta[beta] Peptide Ultra-Sensitive Kit, Meso Scale Discovery, Gaithersburg, Md.). Batch-to-batch conversions were performed as previously described (Clark, supra.).

Blood Genomic DNA Methylation

Whole blood was collected into a 10 ml EDTA tube and mixed by rocking for 5 minutes. Blood was then aliquoted into 2×5 ml and frozen in a 20° C. freezer overnight, then moved to a −80° C. freezer. Samples were thawed and genomic DNA was extracted using the Gentra Puregene Blood kit, following the manufacturer's protocol (Qiagen, Hilden, Germany). Extracted genomic DNA was resolved on a 1% agarose gel to verify that the DNA was of high molecular weight, and was quantified using Qubit™ (Qiagen, Hilden, Germany). Five hundred nanograms of genomic DNA were sodium bisulfite-treated to convert unmethylated cytosines to uracils using the EZ DNA Methylation-Gold™ kit (Zymo Research, Irvine, Calif., USA). The converted DNA was purified and prepared for analysis on the Illumina HumanMethylationEPIC BeadChips™ according to manufacturer protocols (Illumina, San Diego, Calif., USA). In brief, the bisulfite-converted DNA was amplified, fragmented, and hybridized to the HumanMethylationEPIC pool of allele-differentiating oligonucleotides to ensure an equal and random placement of participants and controls on each beadchip. After serial extension, ligation, and cleanup reactions, the DNA was labeled with a fluorescent dye. The labeled DNA was then scanned using an Illumina iScan array scanner. Image analysis, and signal determinations were performed using the GenomeStudio software, Methylation Module (Illumina, San Diego, Calif., USA).

Preprocessing HumanMethylationEPIC Data

Raw intensity data files were imported into R package minfi to assess sample quality, to calculate the detection P-value of each tested probe, and to estimate blood cell counts for each sample (Aryee M J, Jaffe A E, Corrada-Bravo H, Ladd-Acosta C, Feinberg A P, Hansen K D, Irizarry R A (2014) Minfi: a flexible and comprehensive Bioconductor package for the analysis of Infinium DNA methylation microarrays. *Bioinformatics* 30, 1363-1369.). Probes were background- and control-corrected, followed by subset-quantile within array normalization to correct for probe-type bias (Maksimovic J, Gordon L, Oshlack A (2012) SWAN: Subset-quantile within array normalization for illumina infinium HumanMethylation450 BeadChips. *Genome Biol* 13, R44., Wockner L F, Noble E P, Lawford B R, Young R M, Morris C P, Whitehall V L, Voisey J (2014) Genomewide DNA methylation analysis of human brain tissue from schizophrenia patients. *Transl Psychiatry* 4, e339.). Probes were removed from further analysis if: one sample or more exhibited a detection P-value >0.01; the probe contained a single nucleotide polymorphism (SNP); the probe reported methylation at a SNP; the probe was derived from a sex chromosome; the probe measured methylation at a cytosine followed by a nucleotide other than guanine; or the probe is a cross-reactive probe. With these filtration criteria, 97,647 probes were discarded, and 769,190 probes were available for further analysis.

Statistical Analyses

Demographic characteristics from participants with and without LOAD were compared using T-tests with a significance level of P<0.05 adopted for all comparisons. Table 1 indicates those with significance. Methylation levels (i.e., beta-values) were calculated in minfi as the ratio of methylated to total signal (i.e., beta-value=methylated signal/ (methylated signal+unmethylated signal+100)), where beta-values range from 0 (fully unmethylated) to 1 (fully methylated). Beta values were further converted to M-values (i.e., logit-transformed beta-values) for differential analysis to generate M-values appropriate for statistical testing. Linear regression for each tested CpG using a multivariate model was employed using R package limma (Ritchie M E, Phipson B, Wu D, Hu Y, Law C W, Shi W, Smyth G K (2015) limma powers differential expression analyses for RNA-sequencing and microarray studies. *Nucleic Acids Res* 43, e47.), and all discrete (i.e., LOAD vs. no-LOAD) and continuous variables were treated as the independent variable, while methylation level was the dependent variable. A model adjusted for LOAD vs. no-LOAD, sex, age, identification number of the HumanMethylationEPIC array (N=12), and white blood cell counts (i.e., granulocytes, monocytes, natural killer, B-cell, CD8T, and CD4T lymphocytes) was used for regression (Houseman E A, Accomando W P, Koestler D C, Christensen B C, Marsit C J, Nelson H H, Wiencke J K, Kelsey K T (2012) DNA methylation arrays as surrogate measures of cell mixture distribution. *BMC Bioinformatics* 13, 86.). To assess systematic bias of the linear regression model, the genomic inflation factor was calculated for the obtained P-values, yielding a genomic inflation factor of 1.01, thereby suggesting no bias in these methods (Yang J, Weedon M N, Purcell S, Lettre G, Estrada K, Willer C J, Smith A V, Ingelsson E, O'Connell J R, Mangino M, Magi R, Madden P A, Heath A C, Nyholt D R, Martin N G, Montgomery G W, Frayling™, Hirschhorn J N, McCarthy M I, Goddard M E, Visscher P M, Consortium G (2011) Genomic inflation factors under polygenic inheritance. *Eur J Hum Genet* 19, 807-812.). Because methylation levels of immediately flanking probes tested by array-based platforms may exhibit dependence upon one another, and because corrections for multiple testing such as the Benjamini-Hochberg false discovery rate may be inefficient under a varying dependence structure, the R package NHMMfdr was used to detect the adjusted local index of significance (aLIS), an extension of adjusted P-values, for each probe by first converting all P-values to z-scores, followed by using a non-parametric Gaussian mixture distribution with one mixture component, and all other parameters set to default (Kuan P F, Chiang D Y (2012) Integrating prior knowledge in multiple testing under dependence with applications to detecting differential DNA methylation. *Biometrics* 68, 774-783.). An aLIS threshold of <0.05 was used to identify differentially methylated loci. The same multivariate model was used when testing the continuous variables of interest: Rey Auditory Verbal Learning Test (RAVLT), Total Trials and Delayed Recall scores, and Trail Making Test Part B scores (n=38 LOAD, n=39 no-LOAD), and CSF t-tau, p-tau$_{181}$, Abeta$_{42}$, Abeta$_{40}$, levels and t-tau/Abeta$_{42}$, p-tau/Abeta$_{42}$, and Abeta$_{42}$/Abeta$_{40}$ ratios (N=16 LOAD, N=24 no-LOAD).

Results

Participant Characteristics

Table 1 provides demographic characteristics of participants with and without LOAD. LOAD and no-LOAD participants did not differ in age and sex. As expected, CSF values differed between groups.

Genome-Wide DNA Methylation

Of 769,190 loci tested, 477 CpG positions were differentially methylated (Table 2). Classification of the differentially methylated positions to the nearest gene revealed 106 DMP-associated genes, including 21 hypermethylated loci and 97 hypomethylated loci. Twelve genes contained more than one DMP that were hypermethylated and hypomethylated at distinct genomic positions. The mean distance between adjacent hypermethylated and hypomethylated DMPs in the same gene was >500 kilobases. A proportion of DMP-associated genes and their products have been noted by others to participate in LOAD pathogenesis including B3GALT4, FLOTJ, OXT, and DLG2 [Watson, supra, Hondius D C, van Nierop P, Li K W, Hoozemans J J, van der Schors R C, van Haastert E S, van der Vies S M, Rozemuller A J, Smit A B (2016) Profiling the human hippocampal proteome at all pathologic stages of Alzheimer's disease. *Alzheimers Dement* 12, 654-668., Yuyama K, Sun H, Sakai S, Mitsutake S, Okada M, Tahara H, Furukawa J, Fujitani N, Shinohara Y, Igarashi Y (2014) Decreased amyloid-beta pathologies by intracerebral loading of glycosphingolipid-enriched exosomes in Alzheimer model mice. J Biol Chem 289, 24488-24498., Mazurek M F, Beal M F, Bird E D, Martin J B (1987) Oxytocin in Alzheimer's disease: postmortem brain levels. Neurology 37, 1001-1003.

Figure 2A:
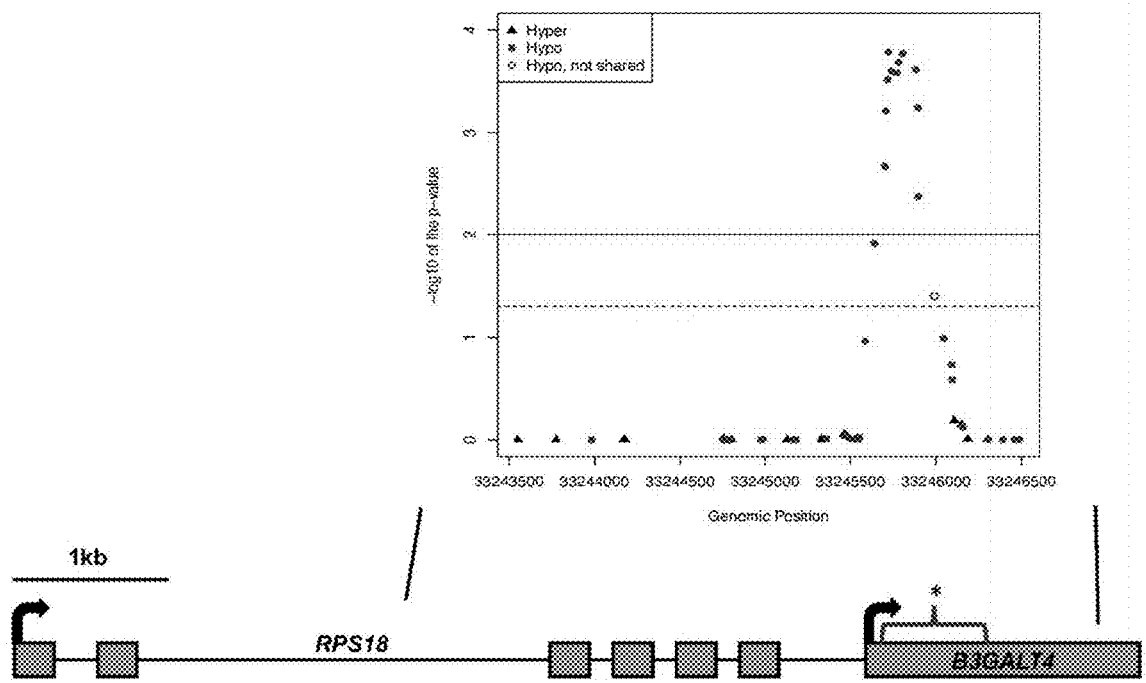
FIGS. 2A-2B.
Figure 2B:
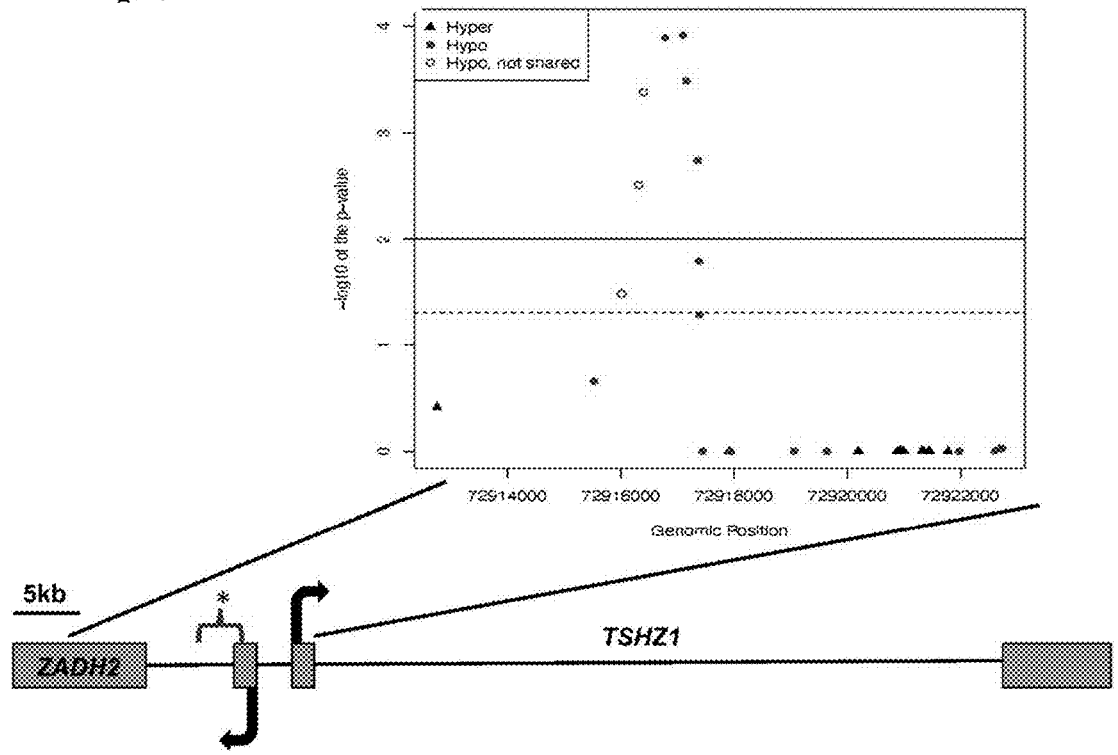
Figure 3:
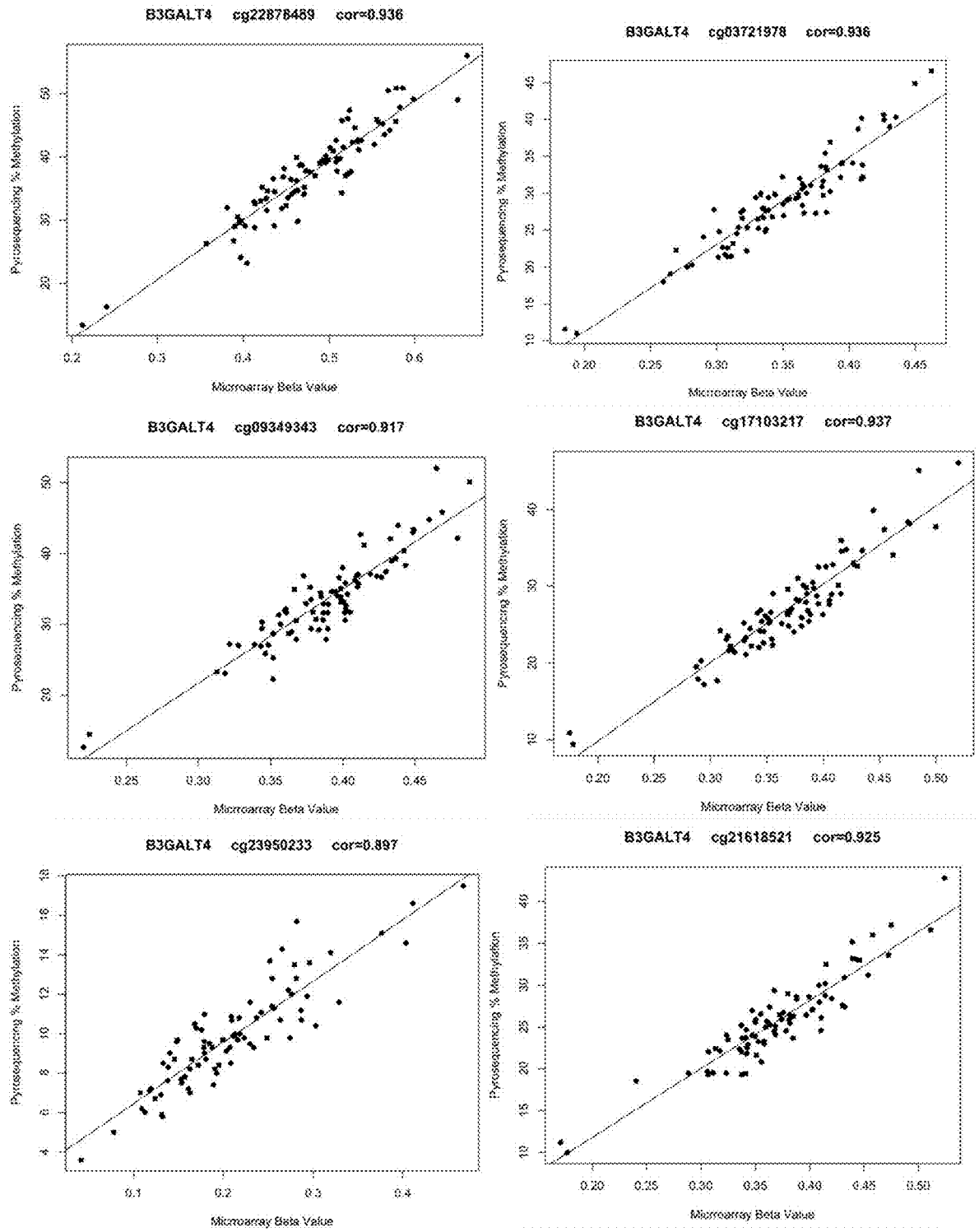
FIG. 3.
Figure 3:
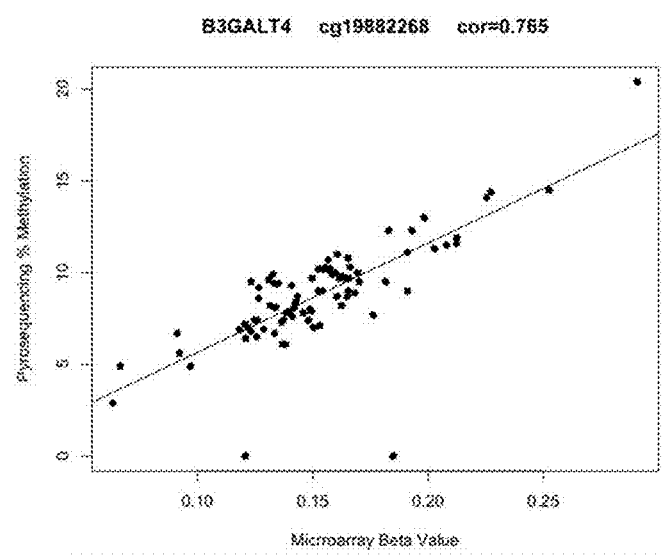
Figure 4:
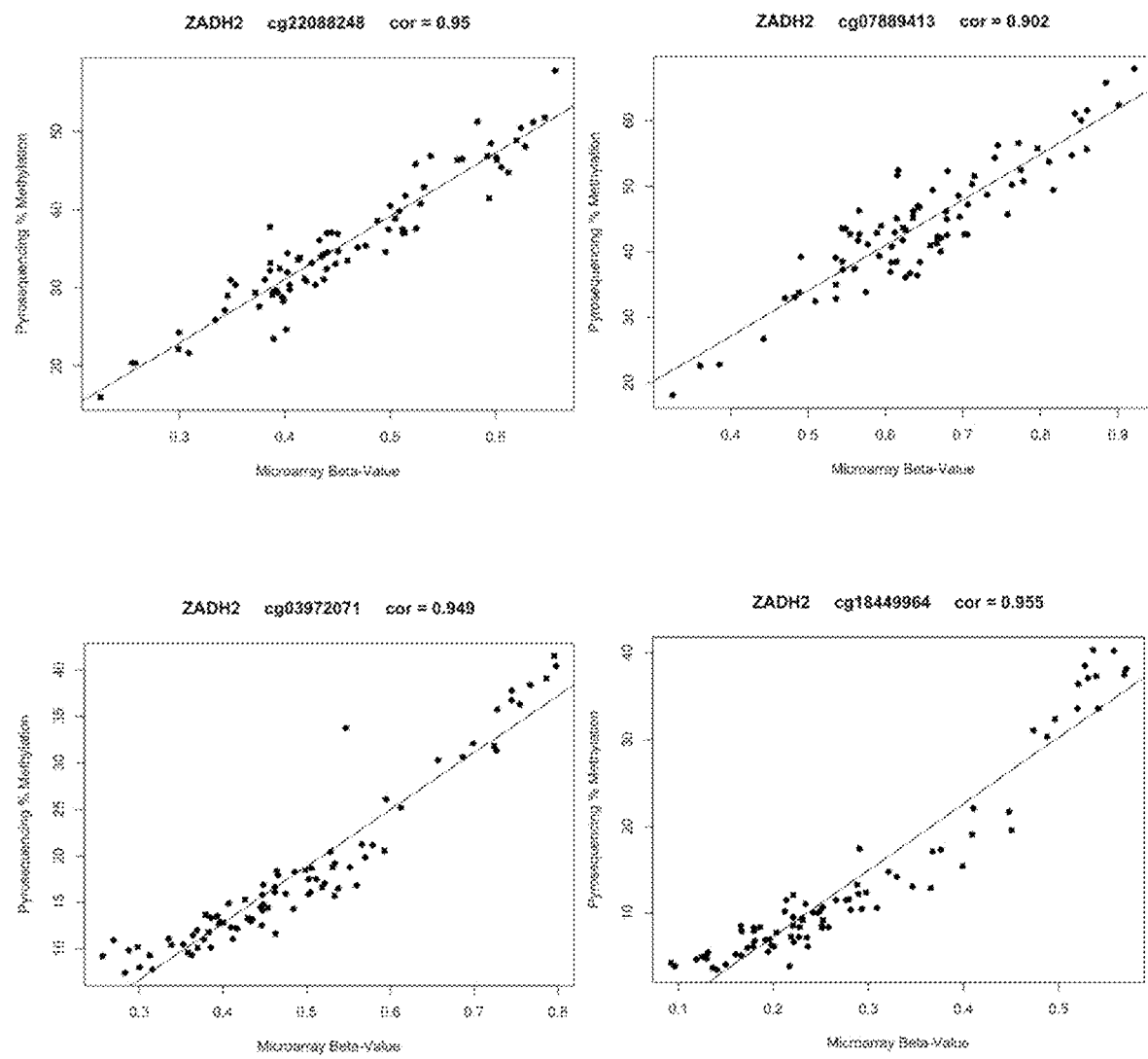
FIG. 4.
Figure 4:
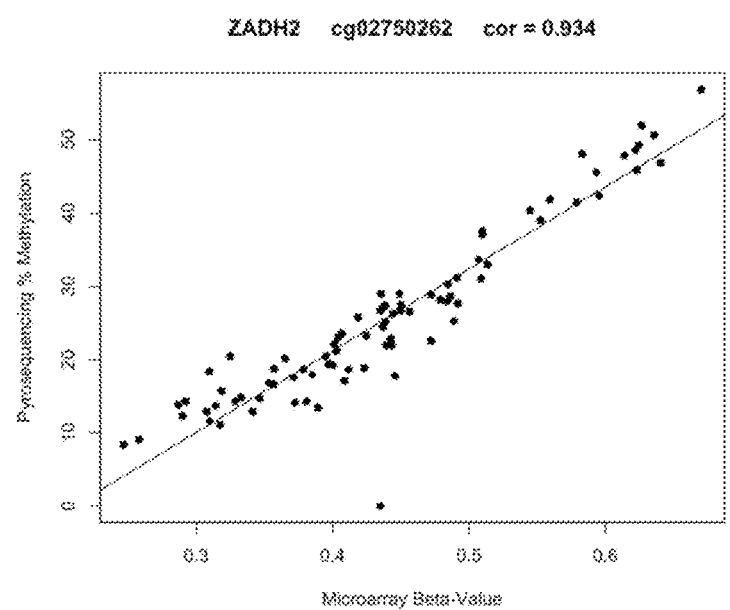

Each comparison of 6 continuous variables comprising RAVLT scores, and CSF t-tau and p-tau$_{181}$ levels, or t-tau/Abeta$_{42}$, p-tau$_{181}$/Abeta$_{42}$, or Abeta$_{42}$/Abeta$_{40}$ ratios yielded a unique set of DMPs. Of the 477 DMPs that distinguished participants with and without LOAD, 17 DMPs were also shared among the 6 continuous variables (FIG. 1). In LOAD patients, 12 of the shared 17 DMPs were hypomethylated in B3GALT4 (Beta-1,3-galatcosyltransferase 4) (EC 2.4.1.62), and 5 were hypomethylated in ZADH2 (Prostaglandin reductase 3) (EC 1.3.1.48) (FIG. 2). Differential levels of DNA methylation at 7 of 7 DMPs at the B3GALT4 locus observed using the HumanMethylationEPIC array was confirmed by pyrosequencing, with a mean correlation coefficient of >0.9 for the 7 DMP sites (FIG. 3). When analyzed as continuous variables, no DMPs associated with TMT-B scores and Abeta$_{42}$ levels were observed that distinguish participants with and without LOAD, and that were shared between the other 6 continuous variables.

Experiments conducted in the course of development of the present invention reveal that LOAD-related DMPs are located throughout the human genome in peripheral blood. In LOAD patients, 17 hypomethylated DMPs in B3GALT4 and ZADH2 are shared with DMPs associated with memory performance, and CSF levels of Abeta and tau. B3GALT4 encodes the enzyme Beta-1,3-galactosyltransferase 4, a type II membrane-bound glycoprotein crucial for the biosynthesis of GM1. GM1 is a ganglioside on the surface of vertebrate cells that participates in the regulation of synaptic transmission in the brain (Sasaki N, Itakura Y, Toyoda M (2015) Ganglioside GM1 Contributes to the State of Insulin Resistance in Senescent Human Arterial Endothelial Cells. *J Biol Chem* 290, 25475-25486., Schnaar R L (2016) Gangliosides of the Vertebrate Nervous System. *J Mol Biol* 428, 3325-3336., Fernandez-Perez E J, Sepulveda F J, Peoples R, Aguayo L G (2017) Role of membrane GM1 on early neuronal membrane actions of Abeta during onset of Alzheimer's disease. *Biochim Biophys Acta* 1863, 3105-3116.). GM1 and other components of the ganglioside biosynthesis pathway are associated with LOAD onset and progression, neuronal cell survival, and neurotoxicity (Fukami Y, Ariga T, Yamada M, Yuki N (2017) Brain Gangliosides in Alzheimer's Disease: Increased Expression of Cholinergic Neuron-Specific Gangliosides. *Curr Alzheimer Res* 14, 586-591., Matsubara T, Nishihara M, Yasumori H, Nakai M, Yanagisawa K, Sato T (2017) Size and Shape of Amyloid Fibrils Induced by Ganglioside Nanoclusters: Role of Sialyl Oligosaccharide in Fibril Formation. *Langmuir* 33, 13874-13881., Liang Y, Ji J, Lin Y, He Y, Liu J (2016) The Ganglioside GM-1 Inhibits Bupivacaine-Induced Neurotoxicity in Mouse Neuroblastoma Neuro2a Cells. *Cell Biochem Funct* 34, 455-462., Kracun I, Kalanj S, Cosovic C, Talan-Hranilovic J (1990) Brain gangliosides in Alzheimer's disease. *J Hirnforsch* 31, 789-793., Yanagisawa K (2015) GM1 ganglioside and Alzheimer's disease. *Glycoconj J* 32, 87-91.). A critical event leading to synaptic failure associated with LOAD is perturbation of neuronal cell membranes resulting from the generation of pore-like structures that jeopardize cell integrity. Synaptotoxicity arises at least in part from lipid raft aggregation of A-beta. (Sepulveda F J, Fierro H, Fernandez E, Castillo C, Peoples R W, Opazo C, Aguayo L G (2014) Nature of the neurotoxic membrane actions of amyloid-beta on hippocampal neurons in Alzheimer's disease. *Neurobiol Aging* 35, 472-481.). Gangliosides including GM1 are concentrated in lipid rafts and interact with Abeta, thereby supporting a role for GM1 and A beat interactions in disruption of neuronal membrane integrity and dysregulation of GM1 biosynthesis by aberrant B3GALT4 expression as contributors to LOAD pathogenesis (Yanagisawa K, Odaka A, Suzuki N, Ihara Y (1995) GM1 ganglioside-bound amyloid beta-protein (A beta): a possible form of preamyloid in Alzheimer's disease. *Nat Med* 1, 1062-1066., Fishman M A, Agrawal H C, Alexander A, Golterman J (1975) Biochemical maturation of human central nervous system myelin. *J Neurochem* 24, 689-694.). A previous study of DNA methylation alterations in the superior temporal gyrus of postmortem LOAD brain samples reported 53 hypermethylated positions in B3GALT4 (Watson, supra.) Twelve of the 53 were those hypomethylated in blood in the present study suggesting an inverse cross-tissue (i.e., brain and blood) correlation with LOAD.

ZADH2 encodes the enzyme zinc binding alcohol dehydrogenase domain containing 2, also referred to as prostaglandin reductase 3 (PGR3). PGR3 is a member of the cyclooxygenase-prostaglandin pathway with a high affinity for 15-keto-PGE2 alpha. (Johansson J U, Woodling N S, Shi J, Andreasson K I (2015) Inflammatory Cyclooxygenase Activity and PGE2 Signaling in Models of Alzheimer's Disease. *Curr Immunol Rev* 11, 125-131., Yagami T, Koma H, Yamamoto Y (2016) Pathophysiological Roles of Cyclooxygenases and Prostaglandins in the Central Nervous System. *Mol Neurobiol* 53, 4754-4771., Johansson J U, Woodling N S, Wang Q, Panchal M, Liang X, Trueba-Saiz A, Brown H D, Mhatre S D, Loui T, Andreasson K I (2015) Prostaglandin signaling suppresses beneficial microglial function in Alzheimer's disease models. *J Clin Invest* 125, 350-364.). The cyclooxygenase-prostaglandin pathway is associated with LOAD risk, particularly PGE2 (Woodling N S, Andreasson K I (2016) Untangling the Web: Toxic and Protective Effects of Neuroinflammation and PGE2 Signaling in Alzheimer's Disease. *ACS Chem Neurosci* 7, 454-463.). Members of the pathway promote pro-inflammatory and anti-inflammatory responses through cell-type-specific G-protein coupled receptors with inhibition of cyclooxygenases reported to decrease LOAD risk (in t' Veld B A, Ruitenberg A, Hofman A, Launer L J, van Duijn C M, Stijnen T, Breteler M M, Stricker B H (2001) Nonsteroidal antiinflammatory drugs and the risk of Alzheimer's disease. *N Engl J Med* 345, 1515-1521., in t' Veld B A, Ruitenberg A, Hofman A, Launer L J, van Duijn C M, Stijnen T, Breteler M M, Stricker B H (2001) Nonsteroidal antiinflammatory drugs and the risk of Alzheimer's disease. *N Engl J Med* 345, 1515-1521., Stewart W F, Kawas C, Corrada M, Metter E J (1997) Risk of Alzheimer's disease and duration of NSAID use. *Neurology* 48, 626-632., Zandi P P, Anthony J C, Hayden K M, Mehta K, Mayer L, Breitner J C, Cache County Study I (2002) Reduced incidence of A D with NSAID but not H2 receptor antagonists: the Cache County Study. *Neurology* 59, 880-886., McGeer P I, Guo J P, Lee M, Kennedy K, McGeer E G (2018) Alzheimer's disease can be spared by nonsteroidal anti-inflammatory drugs. *J Alzheimers Dis* 62, 1219-1222.).

Two online blood-brain DNA methylation comparison instruments were used to interrogate the 12 B3GALT4 DMPs that correlate with LOAD expression in the present data. Lower levels of B3GALT4 DNA methylation in the samples of white blood cells from living patients with LOAD were observed in comparison to samples of postmortem brain tissues from patients who died from LOAD that were used to generate the online instruments (Hannon E, Lunnon K, Schalkwyk L, Mill J (2015) Interindividual methylomic variation across blood, cortex, and cerebellum: implications for epigenetic studies of neurological and neuropsychiatric phenotypes. *Epigenetics* 10, 1024-1032., Edgar R D, Jones M J, Meaney M J, Turecki G, Kobor M S (2017) BECon: a tool for interpreting DNA methylation findings from blood in the context of brain. *Transl Psychiatry* 7, e1187.). Other investigators similarly report discordant DNA methylation profiles between blood and brain tissues associated with other neurological disorders (Farre P, Jones M J, Meaney M J, Emberly E, Turecki G, Kobor M S (2015) Concordant and discordant DNA methylation signatures of aging in human blood and brain. *Epigenetics Chromatin* 8, 19., Walton E, Hass J, Liu J, Roffman J L, Bernardoni F, Roessner V, Kirsch M, Schackert G, Calhoun V, Ehrlich S (2016) Correspondence of DNA Methylation Between Blood and Brain Tissue and Its Application to Schizophrenia Research. *Schizophr Bull* 42, 406-414., Yu L, Chibnik L B, Yang J, McCabe C, Xu J, Schneider J A, D Jager P L, Bennett (2016) Methylation profiles in peripheral blood CD4+ lymphocytes versus brain: The relation to Alzheimer's disease pathology. *Alzheimer's Dement* 12, 942-951.). With regard to the ZADH2 locus, 4 of the 5 DMPs were compared with data from the 450K array used to generate the BECon analysis and the Blood Brain DNA Methylation Comparison Tool (Hannon, supra, Edgar, supra). The 4 DMPs show similar levels of DNA methylation between blood and tissue from diverse brain regions. The $5^{th}$ ZADH2 DMP that is differentially methylated between patients with LOAD and participants without LOAD is a novel probe on the 850K array, and is not interrogated by two online tools. Chouliaras et al. have recently described DMPs in HLA-DPA1/HLA-DPB1, DRC1, PRKAA2, CACLB, CDH2, RTBDN, ZNF256 and SHANK2 genes in the blood of participants with mild cognitive impairment (MCI) based on Montreal Cognitive Assessment (MoCA) scores in comparison to sex-matched cognitively normal participants (Chouliaras L, Kenis G, Visser P J, Scheltens P, Tsolaki M, Jones R W, Kehoe P G, Graff C, Girtler N G, Wallin A K, Rikkert M O, Spiru L, Elias-Sonnenschein L S, Ramakers I H, Pishva E, van Os J, Steinbusch H W, Verhey F R, van den Hove D L, Rutten B P (2015) DNMT3A moderates cognitive decline in subjects with mild cognitive impairment: replicated evidence from two mild cognitive impairment cohorts. *Epigenomics* 7, 533-537.). No DMPs in blood are shared between these observations in participants with MCI and the results of the present investigation of participants with LOAD, suggesting that progression to LOAD exhibits distinct DMP patterns not associated with MCI. Taken together, these data reinforce the use of blood as an accessible tissue of value in the identification of DMPs associated with dementia onset and progression. These data support to the role of enzymes in ganglioside and prostaglandin metabolism in the pathogenesis of Alzheimer's disease, and provide novel diagnostic, prognostic and modifiable therapeutic targets.

In some embodiments, the technology is related to assessing the presence of and methylation state of one or more of the markers identified herein in a biological sample. These markers comprise one or more differentially methylated positions (DMPs) and/or regions (DMRs) as discussed herein, e.g., as provided in FIG. 2. Methylation state is assessed in embodiments of the technology. As such, the technology provided herein is not restricted in the method by which a gene's methylation state is measured. For example, in some embodiments the methylation state is measured by a genome scanning method. For example, one method involves restriction landmark genomic scanning (Kawai et al. (1994) Mol. Cell. Biol. 14: 7421-7427) and another example involves methylation-sensitive arbitrarily primed PCR (Gonzalgo et al. (1997) Cancer Res. 57: 594-599). In some embodiments, changes in methylation patterns at specific CpG sites are monitored by digestion of genomic DNA with methylation-sensitive restriction enzymes followed by Southern analysis of the regions of interest (digestion-Southern method). In some embodiments, analyzing changes in methylation patterns involves a PCR-based process that involves digestion of genomic DNA with methylation-sensitive restriction enzymes prior to PCR amplification (Singer-Sam et al. (1990) Nucl. Acids Res. 18: 687). In addition, other techniques have been reported that utilize bisulfite treatment of DNA as a starting point for methylation analysis. These include methylation-specific PCR (MSP) (Herman et al. (1992) Proc. Natl. Acad. Sci. USA 93: 9821-9826) and restriction enzyme digestion of PCR products amplified from bisulfite-converted DNA (Sadri and Hornsby (1996) Nucl. Acids Res. 24: 5058-5059; and Xiong and Laird (1997) Nucl. Acids Res. 25: 2532-2534). PCR techniques have been developed for detection of gene mutations (Kuppuswamy et al. (1991) Proc. Natl. Acad. Sci. USA 88: 1143-1147) and quantification of allelic-specific expression (Szabo and Mann (1995) Genes Dev. 9: 3097-3108; and Singer-Sam et al. (1992) PCR Methods Appl. 1: 160-163). Such techniques use internal primers, which anneal to a PCR-generated template and terminate immediately 5' of the single nucleotide to be assayed. Methods using a "quantitative MS-SNUPE assay" as described in U.S. Pat. No. 7,037,650 are used in some embodiments.

Upon evaluating a methylation state, the methylation state is often expressed as the fraction or percentage of individual strands of DNA that is methylated at a particular site (e.g., at a single nucleotide, at a particular region or locus, at a longer sequence of interest, e.g., up to a ~100-bp, 200-bp, 500-bp, 1000-bp subsequence of a DNA or longer) relative to the total population of DNA in the sample comprising that particular site. Conventionally, the amount of the unmethylated nucleic acid is determined by PCR using calibrators. Then, a known amount of DNA is bisulfite treated and the resulting methylation-specific sequence is determined using either a real-time PCR or other exponential amplification, e.g., a QuARTS assay (e.g., as provided by U.S. Pat. No. 8,361,720; and U.S. Pat. Appl. Pub. Nos. 2012/0122088 and 2012/0122106).

For example, in some embodiments methods comprise generating a standard curve for the unmethylated target by using external standards. The standard curve is constructed from at least two points and relates the real-time Ct value for unmethylated DNA to known quantitative standards. Then, a second standard curve for the methylated target is constructed from at least two points and external standards. This second standard curve relates the Ct for methylated DNA to known quantitative standards. Next, the test sample Ct values are determined for the methylated and unmethylated populations and the genomic equivalents of DNA are calculated from the standard curves produced by the first two steps. The percentage of methylation at the site of interest is calculated from the amount of methylated DNAs relative to the total amount of DNAs in the population, e.g., (number of methylated DNAs)/(the number of methylated DNAs+number of unmethylated DNAs)×100.

In some embodiments, the methods, compositions, kits and systems of the present invention provide biomarkers for detection, screening, differential diagnosis, monitoring of therapy, and research stratification s in patients with late onset Alzheimer's disease (LOAD), early onset autosomal dominant Alzheimer's disease (ADAD), and/or other neurodegenerative conditions including, for example, Parkinson's disease, Lewy Body Dementia, REM-sleep Behavior Disorder, Huntington's disease, and the like. In certain embodiments, the biomarkers of the present invention are used alone. In other embodiments, the biomarkers are used in panels or subsets of biomarkers. In particular embodiments, the DMP biomarkers of the present invention are used in combination with other biomarkers including, for example, genomic biomarkers, epigenomic biomarkers (e.g., histone modification biomarkers, small RNA biomarkers, chromatin biomarkers, and the like), imaging biomarkers (e.g., MRI and PET biomarkers), cerebrospinal fluid, blood and other body fluid biomarkers (e.g., levels of tau and amyloid), together with clinical signs and symptoms of neurodegeneration (e.g., psychometric tests scores, quality of daily living scores, predictors of predisposing and co-existing conditions such as metabolic syndrome, sleep apnea, history of head trauma, diabetes mellitus, depression, nutritional deficiency, vascular and microvascular disease and the like.)

Also provided herein are compositions and kits for practicing the methods. For example, in some embodiments, reagents (e.g., primers, probes) specific for one or more markers are provided alone or in sets (e.g., sets of primers pairs for amplifying a plurality of markers). Additional reagents for conducting a detection assay may also be provided (e.g., enzymes, buffers, positive and negative controls for conducting QuARTS, PCR, sequencing, bisulfite, or other assays). In some embodiments, the kits containing one or more reagent necessary, sufficient, or useful for conducting a method are provided. Also provided are reaction mixtures containing the reagents. Further provided are master mix reagent sets containing a plurality of reagents that may be added to each other and/or to a test sample to complete a reaction mixture.

In some embodiments, the technology described herein is associated with a programmable machine designed to perform a sequence of arithmetic or logical operations as provided by the methods described herein. For example, some embodiments of the technology are associated with (e.g., implemented in) computer software and/or computer hardware. In one aspect, the technology relates to a computer comprising a form of memory, an element for performing arithmetic and logical operations, and a processing element (e.g., a microprocessor) for executing a series of instructions (e.g., a method as provided herein) to read, manipulate, and store data. In some embodiments, a microprocessor is part of a system for determining a methylation state (e.g., of one or more DMPs as provided in FIG. 2); comparing methylation states (e.g., of one or more DMPs as provided in FIG. 2); generating standard curves; determining a Ct value; calculating a fraction, frequency, or percentage of methylation (e.g., of one or more DMPs as provided in FIG. 2); identifying a CpG island; determining a specificity and/or sensitivity of an assay or marker; calculating an ROC curve and an associated AUC; sequence analysis; all as described herein or is known in the art.

In some embodiments, a microprocessor or computer uses methylation state data in an algorithm to predict Alzheimer's disease or other neurodegenerative disease e.g., Parkinson's disease, Lewy Body Dementia, REM-sleep Behavior Disorder, Huntington's disease, and the like.

In some embodiments, a software or hardware component receives the results of multiple assays and determines a single value result to report to a user that indicates a risk for Alzheimer's disease based on the results of the multiple assays (e.g., determining the methylation state of multiple DMPs and DMRs, e.g., as provided in FIG. 2). Related embodiments calculate a risk factor based on a mathematical combination (e.g., a weighted combination, a linear combination) of the results from multiple assays, e.g., determining the methylation states of multiple markers (such as multiple DMPs and DMRs as provided in FIG. 2). In some embodiments, the methylation state of a DMP and/or defines a dimension and may have values in a multidimensional space and the coordinate defined by the methylation states of multiple DMR is a result, e.g., to report to a user, e.g., related to an Alzheimer's disease risk.

Some embodiments comprise a storage medium and memory components. Memory components (e.g., volatile and/or nonvolatile memory) find use in storing instructions (e.g., an embodiment of a process as provided herein) and/or data (e.g., a work piece such as methylation measurements, sequences, and statistical descriptions associated therewith). Some embodiments relate to systems also comprising one or more of a CPU, a graphics card, and a user interface (e.g., comprising an output device such as display and an input device such as a keyboard).

Programmable machines associated with the technology comprise conventional extant technologies and technologies in development or yet to be developed (e.g., a quantum computer, a chemical computer, a DNA computer, an optical computer, a spintronics based computer, etc.).

In some embodiments, the technology comprises a wired (e.g., metallic cable, fiber optic) or wireless transmission medium for transmitting data. For example, some embodiments relate to data transmission over a network (e.g., a local area network (LAN), a wide area network (WAN), an ad-hoc network, the internet, etc.). In some embodiments, programmable machines are present on such a network as peers and in some embodiments the programmable machines have a client/server relationship.

In some embodiments, data are stored on a computer-readable storage medium such as a hard disk, flash memory, optical media, a floppy disk, etc.

In some embodiments, the technology provided herein is associated with a plurality of programmable devices that operate in concert to perform a method as described herein. For example, in some embodiments, a plurality of computers (e.g., connected by a network) may work in parallel to collect and process data, e.g., in an implementation of cluster computing or grid computing or some other distributed computer architecture that relies on complete computers (with onboard CPUs, storage, power supplies, network interfaces, etc.) connected to a network (private, public, or the internet) by a conventional network interface, such as Ethernet, fiber optic, or by a wireless network technology.

For example, some embodiments provide a computer that includes a computer-readable medium. The embodiment includes a random-access memory (RAM) coupled to a processor. The processor executes computer-executable program instructions stored in memory. Such processors may include a microprocessor, an ASIC, a state machine, or other processor, and can be any of a number of computer processors, such as processors from Intel Corporation of Santa Clara, Calif. and Motorola Corporation of Schaumburg, Ill. Such processors include, or may be in communication with, media, for example computer-readable media, which stores instructions that, when executed by the processor, cause the processor to perform the steps described herein.

Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any suitable computer-programming language, including, for example, C, C++, C #, Visual Basic, Java, Python, Perl, and JavaScript.

Computers are connected in some embodiments to a network. Computers may also include a number of external or internal devices such as a mouse, a CD-ROM, DVD, a keyboard, a display, or other input or output devices. Examples of computers are personal computers, digital assistants, personal digital assistants, cellular phones, mobile phones, smart phones, pagers, digital tablets, laptop computers, internet appliances, and other processor-based devices. In general, the computers related to aspects of the technology provided herein may be any type of processor-based platform that operates on any operating system, such as Microsoft Windows, Linux, UNIX, Mac OS X, etc., capable of supporting one or more programs comprising the technology provided herein. Some embodiments comprise a personal computer executing other application programs (e.g., applications). The applications can be contained in memory and can include, for example, a word processing application, a spreadsheet application, an email application, an instant messenger application, a presentation application, an Internet browser application, a calendar/organizer application, and any other application capable of being executed by a client device.

All such components, computers, and systems described herein as associated with the technology may be logical or virtual and/or consensual.

Accordingly, provided herein is technology related to a method of screening for Alzheimer's disease in a sample obtained from a subject, the method comprising assaying a methylation state of a marker in a sample obtained from a subject; and identifying the subject as having Alzheimer's disease when the methylation state of the marker is different than a methylation state of the marker assayed in a subject that does not have a Alzheimer's disease, wherein the marker comprises a differentially methylated position (DMP) in a differentially methylated region (DMR) as provided in FIG. 2.

The technology is not limited in the methylation state assessed. In some embodiments assessing the methylation state of the marker in the sample comprises determining the methylation state of one base. In some embodiments, assaying the methylation state of the marker in the sample comprises determining the extent of methylation at a plurality of bases. Moreover, in some embodiments the methylation state of the marker comprises an increased methylation of the marker relative to a normal methylation state of the marker. In some embodiments, the methylation state of the marker comprises a decreased methylation of the marker relative to a normal methylation state of the marker. In some embodiments the methylation state of the marker comprises a different pattern of methylation of the marker relative to a normal methylation state of the marker.

Furthermore, in some embodiments the marker is a region of 100 or fewer bases, the marker is a region of 500 or fewer bases, the marker is a region of 1000 or fewer bases, the marker is a region of 5000 or fewer bases, or, in some embodiments, the marker is one base. In some embodiments the marker is in a high CpG density promoter.

The technology is not limited by sample type. For example, in some embodiments the sample is a blood sample (e.g., plasma, serum, whole blood), a tissue sample (e.g., brain tissue), an excretion, a urine sample, a saliva sample, a cerebrospinal fluid (CSF) sample, or a cheek swab sample.

Furthermore, the technology is not limited in the method used to determine methylation state. In some embodiments the assaying comprises using methylation specific polymerase chain reaction, nucleic acid sequencing, mass spectrometry, methylation specific nuclease, mass-based separation, or target capture. In some embodiments, the assaying comprises use of a methylation specific oligonucleotide. In some embodiments, the technology uses massively parallel sequencing (e.g., next-generation sequencing) to determine methylation state, e.g., sequencing-by-synthesis, real-time (e.g., single-molecule) sequencing, bead emulsion sequencing, nanopore sequencing, etc.

The technology provides reagents for detecting a DMP and/or DMR, e.g., in some embodiments are provided a set of oligonucleotides. In some embodiments are provided an oligonucleotide comprising a sequence complementary to a chromosomal region having a base in a DMR, e.g., an oligonucleotide sensitive to methylation state of a DMR.

The technology provides various panels of markers, e.g., in some embodiments the marker comprises a chromosomal region having an annotation that is B3GALT4 and/or ZADH2. In addition, embodiments provide a method of analyzing a DMP and/or DMR from FIG. 2.

Kit embodiments are provided, e.g., a kit comprising a bisulfite reagent; and a control nucleic acid comprising a sequence from a DMP and/or DMR selected from a group consisting of FIG. 2, and having a methylation state associated with a subject who does not have Alzheimer's disease. In some embodiments, kits comprise a bisulfite reagent and an oligonucleotide as described herein. In some embodiments, kits comprise a bisulfite reagent; and a control nucleic acid comprising a sequence from a DMP and/or DMR selected from FIG. 2 and having a methylation state associated with a subject who has Alzheimer's disease. Some kit embodiments comprise a sample collector for obtaining a sample from a subject; reagents for isolating a nucleic acid from the sample; a bisulfite reagent; and an oligonucleotide as described herein.

The technology is related to embodiments of compositions (e.g., reaction mixtures). In some embodiments are provided a composition comprising a nucleic acid comprising a DMR and a bisulfite reagent. Some embodiments provide a composition comprising a nucleic acid comprising a DMR and an oligonucleotide as described herein. Some embodiments provide a composition comprising a nucleic acid comprising a DMR and a methylation-sensitive restriction enzyme. Some embodiments provide a composition comprising a nucleic acid comprising a DMR and a polymerase.

Additional related method embodiments are provided for screening for Alzheimer's disease in a sample obtained from a subject, e.g., a method comprising determining a methylation state of a marker in the sample comprising a base in a DMR that as shown in FIG. 2., comparing the methylation state of the marker from the subject sample to a methylation state of the marker from a normal control sample from a subject who does not have a Alzheimer's disease; and determining a confidence interval and/or a p value of the difference in the methylation state of the subject sample and the normal control sample. In some embodiments, the confidence interval is 90%, 95%, 97.5%, 98%, 99%, 99.5%, 99.9% or 99.99% and the p value is 0.1, 0.05, 0.025, 0.02, 0.01, 0.005, 0.001, or 0.0001. Some embodiments of methods provide steps of reacting a nucleic acid comprising a DMP and/or DMR with a bisulfite reagent to produce a bisulfite-reacted nucleic acid; sequencing the bisulfite-reacted nucleic acid to provide a nucleotide sequence of the bisulfite-reacted nucleic acid; comparing the nucleotide sequence of the bisulfite-reacted nucleic acid with a nucleotide sequence of a nucleic acid comprising the DMP and/or DMR from a subject who does not have Alzheimer's disease to identify differences in the two sequences; and identifying the subject as having Alzheimer's disease when a difference is present.

Systems for screening for Alzheimer's disease in a sample obtained from a subject are provided by the technology. Exemplary embodiments of systems include, e.g., a system for screening for Alzheimer's disease in a sample obtained from a subject, the system comprising an analysis component configured to determine the methylation state of a sample, a software component configured to compare the methylation state of the sample with a control sample or a reference sample methylation state recorded in a database, and an alert component configured to alert a user of an Alzheimer's-associated methylation state. An alert is determined in some embodiments by a software component that receives the results from multiple assays (e.g., determining the methylation states of multiple markers, e.g., a DMP and/or DMR provided in FIG. 2), and calculating a value or result to report based on the multiple results. Some embodiments provide a database of weighted parameters associated with each DMP and/or DMR provided herein for use in calculating a value or result and/or an alert to report to a user (e.g., such as a physician, nurse, clinician, etc.). In some embodiments all results from multiple assays are reported and in some embodiments one or more results are used to provide a score, value, or result based on a composite of one or more results from multiple assays that is indicative of Alzheimer's disease risk in a subject.

In some embodiments of systems, a sample comprises a nucleic acid comprising a DMP or DMR. In some embodiments the system further comprises a component for isolating a nucleic acid, a component for collecting a sample such as a component for collecting a blood sample. In some embodiments, the system comprises nucleic acid sequences comprising a DMP or a DMR. In some embodiments the database comprises nucleic acid sequences from subjects who do not have Alzheimer's disease. Also provided are nucleic acids, e.g., a set of nucleic acids, each nucleic acid having a sequence comprising a DMP or DMR. In some embodiments the set of nucleic acids wherein each nucleic acid has a sequence from a subject who does not have Alzheimer's disease. Related system embodiments comprise a set of nucleic acids as described and a database of nucleic acid sequences associated with the set of nucleic acids. Some embodiments further comprise a bisulfite reagent. Further embodiments comprise a nucleic acid sequencer.

Additional embodiments will be apparent to persons skilled in the relevant art based on the teachings contained herein. All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

TABLE 1

Sample and biomarker characteristic means and standard deviations in parentheses

|  | LOAD | No-LOAD | T-test or chi-square |
|---|---|---|---|
| N | 45 | 39 | |
| Age (years) | 73.56 (6.8) | 75.33 (6.0) | $t = -1.27$, $p = 0.21$ |
| Sex | 22 M; 23 F | 18 M; 21 F | $X^2 = 0.06$, $p = 0.80$ |
| Education (years) | 14.6 (2.3) | 16.6 (3.0) | $t = 3.32$, $p = 0.001$ |
| $A\beta_{42}$ (ln)[1] (pg/mL) | 6.02 (0.4) | 6.65 (0.3) | $t = 5.56$, $p < 0.001$ |
| $A\beta_{42}/A\beta_{40}$[1] | 0.06 (0.02) | 0.10 (0.02) | $t = 4.66$, $p < 0.001$ |
| t-tau[1] (pg/mL) | 806.67 (361.7) | 454.11 (199.0) | $t = -3.56$, $p = 0.002$ |
| p-tau$_{181}$[1] (pg/mL) | 79.84 (29.0) | 56.6 (19.9) | $t = -3.01$, $p = 0.005$ |
| t-tau/$A\beta_{42}$[1] (pg/mL) | 2.05 (0.9) | 0.64 (0.4) | $t = -5.98$, $p < 0.001$ |
| p-tau$_{181}$/$A\beta42$[1] (pg/mL) | 0.20 (0.1) | 0.08 (0.1) | $t = -6.02$, $p < 0.001$ |

[1]CSF sample n = 40 (n = 16 LOAD and n = 24 no-LOAD controls)

TABLE 2

LOAD vs. no-LOAD differentially methylated positions

| CpG ID | Chromosome | Position | Gene Symbol(s) | Mean Beta Difference (Control-AD) |
|---|---|---|---|---|
| cg06193043 | 1 | 11908199 | NPPA | 0.0296 |
| cg24844545 | 1 | 11908347 | NPPA | 0.0224 |
| cg08075305 | 1 | 11908418 | NPPA | 0.0107 |
| cg09514626 | 1 | 11908659 | NPPA | 0.0296 |
| cg24435407 | 1 | 11909677 | | 0.0104 |
| cg22943795 | 1 | 15497993 | C1orf195 TMEM51 | 0.0145 |
| cg09592954 | 1 | 15498143 | TMEM51 C1orf195 | 0.0169 |
| cg01244557 | 1 | 15498257 | C1orf195 TMEM51 | 0.0121 |
| cg10001905 | 1 | 15498298 | TMEM51 C1orf195 | 0.0117 |
| cg09003612 | 1 | 43425222 | SLC2A1 SLC2A1-AS1 | 0.0447 |
| cg00102166 | 1 | 43425337 | SLC2A1 | 0.0272 |
| cg09358973 | 1 | 201618030 | NAV1 | 0.0418 |
| cg14920846 | 1 | 201618209 | NAV1 | 0.0534 |
| cg19827875 | 1 | 201618284 | NAV1 | 0.0275 |
| cg07599786 | 1 | 201618654 | NAV1 | 0.0606 |
| cg04179952 | 1 | 201619295 | NAV1 | 0.0723 |
| cg04287574 | 1 | 201619622 | NAV1 | 0.0669 |
| cg12454169 | 2 | 30669597 | LCLAT1 | 0.0559 |
| cg10326673 | 2 | 30669757 | LCLAT1 | 0.1188 |
| cg15652532 | 2 | 30669759 | LCLAT1 | 0.1059 |
| cg10792309 | 2 | 97505416 | ANKRD23 | 0.0117 |
| cg07490070 | 2 | 97505464 | ANKRD23 | 0.0380 |
| cg03997390 | 2 | 201170790 | SPATS2L | 0.0194 |
| cg18609578 | 2 | 201170806 | SPATS2L | 0.0218 |
| cg14214239 | 2 | 201170828 | SPATS2L | 0.0120 |
| cg01565529 | 2 | 206628415 | NRP2 | −0.0515 |
| cg04088940 | 2 | 206628454 | NRP2 | −0.0344 |
| cg22308949 | 2 | 206628553 | NRP2 | −0.0362 |
| cg05348875 | 2 | 206628625 | NRP2 | −0.0373 |
| cg14157435 | 2 | 206628692 | NRP2 | −0.0472 |
| cg10126788 | 2 | 206628727 | NRP2 | −0.0390 |
| cg20351668 | 2 | 206628737 | NRP2 | −0.0493 |
| cg25715429 | 2 | 206628747 | NRP2 | −0.0468 |
| cg10807027 | 2 | 206628773 | NRP2 | −0.0477 |
| cg24086040 | 2 | 241458939 | ANKMY1 | 0.0142 |
| cg24539848 | 2 | 241458974 | ANKMY1 | 0.0283 |
| cg08461339 | 2 | 241459227 | ANKMY1 | 0.0361 |
| cg08276645 | 2 | 241459502 | ANKMY1 | 0.0507 |
| cg16909733 | 2 | 241459847 | ANKMY1 | 0.0179 |
| cg03743720 | 2 | 241460002 | ANKMY1 | 0.0325 |
| cg07378821 | 3 | 39425509 | SLC25A38 | 0.0243 |
| cg26410105 | 3 | 39425775 | SLC25A38 | 0.0254 |
| cg20180092 | 3 | 39425780 | SLC25A38 | 0.0214 |
| cg03206717 | 3 | 39425978 | SLC25A38 | 0.0192 |
| cg16320329 | 3 | 45981161 | FYCO1 | 0.0155 |
| cg27123613 | 3 | 45982438 | FYCO1 | 0.0026 |
| cg08033130 | 3 | 45983597 | CXCR6 FYCO1 | −0.0728 |
| cg19145607 | 3 | 45983792 | FYCO1 CXCR6 | −0.0382 |
| cg07983767 | 3 | 45984158 | FYCO1 CXCR6 | −0.0404 |
| cg23025798 | 3 | 113155528 | CFAP44 | 0.0086 |
| cg05709162 | 3 | 113160071 | WDR52 | 0.0095 |
| cg03552293 | 3 | 113160183 | WDR52 | 0.0198 |
| cg15044041 | 3 | 113160313 | WDR52 | 0.0215 |
| cg24199400 | 3 | 113160430 | WDR52 | 0.0202 |

TABLE 2-continued

LOAD vs. no-LOAD differentially methylated positions

| CpG ID | Chromosome | Position | Gene Symbol(s) | Mean Beta Difference (Control-AD) |
|---|---|---|---|---|
| cg11921736 | 3 | 113160437 | WDR52 | 0.0287 |
| cg07128416 | 3 | 113160490 | WDR52 | 0.0449 |
| cg12856970 | 3 | 113160531 | CFAP44 | 0.0449 |
| cg07054641 | 3 | 113160554 | WDR52 | 0.0188 |
| cg08516817 | 3 | 113160623 | WDR52 | 0.0234 |
| cg04653021 | 3 | 122514541 | DIRC2 | 0.0210 |
| cg02814805 | 3 | 122514629 | DIRC2 | 0.0330 |
| cg05328359 | 3 | 122514679 | DIRC2 | 0.0312 |
| cg08398359 | 3 | 122514784 | DIRC2 | 0.0343 |
| cg10627428 | 3 | 122514814 | DIRC2 | 0.0312 |
| cg00299558 | 3 | 183958478 | VWA5B2 MIR1224 | 0.0546 |
| cg17009978 | 3 | 183959000 | VWA5B2 MIR1224 | 0.0160 |
| cg12821315 | 3 | 183959034 | VWA5B2 MIR1224 | 0.0138 |
| cg03981074 | 3 | 183959062 | MIR1224 VWA5B2 | 0.0119 |
| cg09618015 | 3 | 183959073 | VWA5B2 MIR1224 | 0.0159 |
| cg04086468 | 3 | 185911208 | DGKG | 0.0026 |
| cg17802213 | 3 | 185911316 | DGKG | 0.0173 |
| cg17293936 | 3 | 185911519 | DGKG | 0.0249 |
| cg04391718 | 3 | 185911702 | DGKG | 0.0140 |
| cg12121643 | 3 | 185911796 | DGKG | 0.0326 |
| cg24155429 | 3 | 185911885 | DGKG | 0.0185 |
| cg15709989 | 3 | 185912227 | DGKG | 0.0135 |
| cg02749735 | 3 | 185912253 | DGKG | 0.0086 |
| cg18172135 | 3 | 185912486 | DGKG | 0.0024 |
| cg22066108 | 4 | 3534761 | LRPAP1 | 0.0225 |
| cg25201363 | 4 | 3534845 | LRPAP1 | 0.0351 |
| cg16511795 | 4 | 3535009 | LRPAP1 | 0.0327 |
| cg15362380 | 4 | 3535519 | LRPAP1 | −0.0104 |
| cg27434509 | 4 | 5710337 | EVC2 | 0.0283 |
| cg17255450 | 4 | 5710372 | EVC2 | 0.0166 |
| cg06426416 | 4 | 5710403 | EVC2 | 0.0248 |
| cg05542338 | 4 | 5710407 | EVC2 PCDHGA4 PCDHGA12 PCDHGA5 PCDHGB3 PCDHGA3 PCDHGA6 PCDHGB6 PCDHGB1 PCDHGB2 PCDHGB4 PCDHGA11 PCDHGA10 PCDHGB5 PCDHGA9 PCDHGA7 PCDHGA1 PCDHGA2 PCDHGB7 | 0.0245 |
| cg07802710 | 5 | 140810260 | PCDHGA8 PCDHGA5 PCDHGA12 PCDHGA4 PCDHGB4 PCDHGB2 PCDHGB1 PCDHGB6 PCDHGA6 PCDHGA3 PCDHGB3 PCDHGA9 PCDHGB5 PCDHGA10 PCDHGA11 PCDHGB7 PCDHGA8 PCDHGA2 PCDHGA1 | 0.0199 |
| cg02267483 | 5 | 140810404 | PCDHGA7 PCDHGB4 PCDHGB6 PCDHGB1 PCDHGB2 PCDHGB3 PCDHGA6 PCDHGA3 PCDHGA5 PCDHGA12 PCDHGA4 PCDHGA8 PCDHGB7 PCDHGA1 PCDHGA2 PCDHGA7 PCDHGA9 PCDHGB5 PCDHGA10 | 0.0357 |
| cg21185686 | 5 | 140810433 | PCDHGA11 PCDHGB4 PCDHGB3 PCDHGA6 PCDHGA3 PCDHGB6 PCDHGB1 PCDHGB2 PCDHGA5 PCDHGA4 PCDHGA12 PCDHGA8 PCDHGB7 PCDHGA7 PCDHGA1 PCDHGA2 PCDHGA10 PCDHGB5 PCDHGA9 | 0.0191 |
| cg14253517 | 5 | 140810726 | PCDHGA11 PCDHGA11 PCDHGA9 PCDHGB5 PCDHGA10 PCDHGA1 PCDHGA2 | 0.0204 |

TABLE 2-continued

LOAD vs. no-LOAD differentially methylated positions

| CpG ID | Chromosome | Position | Gene Symbol(s) | Mean Beta Difference (Control-AD) |
|---|---|---|---|---|
| cg22151446 | 5 | 140810805 | PCDHGA7 PCDHGA8 PCDHGB7 PCDHGA12 PCDHGA4 PCDHGA5 PCDHGB6 PCDHGB2 PCDHGB1 PCDHGB3 PCDHGA6 PCDHGA3 PCDHGB4 PCDHGA12 PCDHGA4 PCDHGA5 PCDHGB2 PCDHGB1 PCDHGB6 PCDHGA6 PCDHGA3 PCDHGB3 PCDHGB4 PCDHGA11 PCDHGA9 PCDHGB5 PCDHGA10 PCDHGA2 PCDHGA1 PCDHGA7 PCDHGB7 | 0.0273 |
| cg09639151 | 5 | 140810920 | PCDHGA8 | 0.0258 |
| cg09604094 | 5 | 173236266 | | 0.0224 |
| cg19852286 | 5 | 173237320 | | 0.0152 |
| cg24758392 | 5 | 180396687 | | 0.0553 |
| cg17221856 | 5 | 180396891 | | 0.0948 |
| cg14457074 | 5 | 180408785 | | 0.1040 |
| cg25366315 | 5 | 180408809 | | 0.1424 |
| cg24157836 | 5 | 180414896 | BTNL3 | 0.0942 |
| cg17876578 | 6 | 291859 | DUSP22 | 0.0361 |
| cg21548813 | 6 | 291882 | DUSP22 | 0.0489 |
| cg03395511 | 6 | 291903 | DUSP22 | 0.0451 |
| cg18110333 | 6 | 292329 | DUSP22 | 0.0637 |
| cg05064044 | 6 | 292385 | DUSP22 | 0.0579 |
| cg11235426 | 6 | 292522 | DUSP22 | 0.0306 |
| cg01516881 | 6 | 292596 | DUSP22 | 0.0456 |
| cg26668828 | 6 | 292823 | DUSP22 | 0.0207 |
| cg01171360 | 6 | 293285 | DUSP22 | 0.0232 |
| cg10270150 | 6 | 297974 | DUSP22 | −0.0039 |
| cg21296693 | 6 | 4359898 | | 0.0061 |
| cg15292507 | 6 | 4362795 | | 0.0316 |
| cg16747928 | 6 | 4370460 | | −0.0256 |
| cg21802947 | 6 | 4372407 | | −0.0046 |
| cg27315841 | 6 | 4378675 | | −0.0012 |
| cg09422301 | 6 | 24494043 | ALDH5A1 | 0.0481 |
| cg06752595 | 6 | 24494082 | ALDH5A1 | 0.0789 |
| cg18395531 | 6 | 24494605 | ALDH5A1 | 0.0271 |
| cg25375764 | 6 | 24494665 | ALDH5A1 | 0.0109 |
| cg11517269 | 6 | 28058789 | ZSCAN12L1 | 0.0330 |
| cg12623302 | 6 | 28058802 | ZSCAN12L1 | 0.0314 |
| cg18105139 | 6 | 28058856 | ZSCAN12L1 | 0.0267 |
| cg17849569 | 6 | 28058911 | ZSCAN12L1 | 0.0339 |
| cg02631126 | 6 | 28058918 | ZSCAN12L1 | 0.0384 |
| cg01354632 | 6 | 28058969 | ZSCAN12P1 | 0.0410 |
| cg12740337 | 6 | 28058973 | ZSCAN12L1 | 0.0320 |
| cg24100115 | 6 | 30698584 | FLOT1 | 0.0115 |
| cg02684104 | 6 | 30698706 | FLOT1 | 0.0158 |
| cg04353171 | 6 | 30698729 | FLOT1 | 0.0152 |
| cg05681859 | 6 | 30698734 | FLOT1 | 0.0278 |
| cg18760837 | 6 | 30698777 | FLOT1 | 0.0106 |
| cg17988780 | 6 | 30698780 | FLOT1 | 0.0123 |
| cg19448318 | 6 | 30698784 | FLOT1 | 0.0104 |
| cg16254746 | 6 | 30698843 | FLOT1 | 0.0098 |
| cg10513302 | 6 | 30698905 | FLOT1 | 0.0063 |
| cg27071793 | 6 | 31275718 | | −0.0558 |
| cg27258561 | 6 | 31275767 | | −0.0540 |
| cg12076350 | 6 | 31275791 | | −0.0647 |
| cg02446475 | 6 | 31275807 | | −0.0786 |
| cg17250082 | 6 | 31275875 | | −0.0786 |
| cg08762424 | 6 | 31275881 | | −0.0771 |
| cg03127244 | 6 | 33245638 | B3GALT4 | 0.0138 |
| cg22878489 | 6 | 33245701 | B3GALT4 | 0.0243 |
| cg03721978 | 6 | 33245706 | B3GALT4 | 0.0097 |
| cg09349343 | 6 | 33245717 | B3GALT4 | 0.0068 |
| cg17103217 | 6 | 33245721 | B3GALT4 | 0.0163 |
| cg23950233 | 6 | 33245739 | B3GALT4 | 0.0218 |
| cg21618521 | 6 | 33245770 | B3GALT4 | 0.0116 |
| cg19882268 | 6 | 33245779 | B3GALT4 | 0.0117 |
| cg00052772 | 6 | 33245804 | B3GALT4 | 0.0108 |
| cg27147350 | 6 | 33245881 | B3GALT4 | 0.0103 |

TABLE 2-continued

LOAD vs. no-LOAD differentially methylated positions

| CpG ID | Chromosome | Position | Gene Symbol(s) | Mean Beta Difference (Control-AD) |
|---|---|---|---|---|
| cg06362282 | 6 | 33245893 | B3GALT4 | 0.0241 |
| cg24605046 | 6 | 33245895 | B3GALT4 | 0.0265 |
| cg26055446 | 6 | 33245990 | B3GALT4 | 0.0050 |
| cg22795331 | 6 | 117785611 |  | −0.0315 |
| cg00258203 | 6 | 117801545 |  | 0.0101 |
| cg01883195 | 6 | 117802401 | DCBLD1 | 0.0207 |
| cg07643096 | 6 | 117802588 | DCBLD1 | 0.0092 |
| cg27642470 | 6 | 117802710 | DCBLD1 | 0.0149 |
| cg11412288 | 6 | 117802725 | DCBLD1 | 0.0354 |
| cg23172480 | 6 | 117802786 | DCBLD1 | 0.0127 |
| cg12444861 | 6 | 144386275 | PLAGL1 | 0.0299 |
| cg02849309 | 6 | 144386280 | PLAGL1 | 0.0191 |
| cg01595870 | 6 | 144386416 | PLAGL1 | 0.0311 |
| cg09293391 | 6 | 144386418 | PLAGL1 | 0.0271 |
| cg25291978 | 6 | 144386422 | PLAGL1 | 0.0089 |
| cg08224159 | 6 | 151646312 | AKAP12 | −0.0103 |
| cg15892964 | 6 | 151646540 | AKAP12 | −0.0176 |
| cg04221606 | 6 | 151646552 | AKAP12 | −0.0195 |
| cg24322333 | 6 | 151646584 | AKAP12 | −0.0110 |
| cg03446012 | 6 | 151646601 | AKAP12 | −0.0191 |
| cg18245460 | 6 | 151646651 | AKAP12 | −0.0058 |
| cg12794224 | 6 | 151646761 | AKAP12 | −0.0127 |
| cg25855249 | 6 | 151646817 | AKAP12 | −0.0182 |
| cg06019170 | 6 | 151646957 | AKAP12 | −0.0170 |
| cg23078220 | 7 | 73507353 | LIMK1 | 0.0285 |
| cg23722096 | 7 | 127347748 | SND1 | −0.0030 |
| cg02757031 | 7 | 127349246 | SND1 | 0.0035 |
| cg26769934 | 7 | 127351990 | SND1 | −0.0072 |
| cg01649459 | 7 | 127357737 | SND1 | 0.0216 |
| cg01460622 | 7 | 127358416 | SND1 | 0.0054 |
| cg25039158 | 7 | 127365616 | SND1 | 0.0049 |
| cg23455837 | 7 | 157809325 | PTPRN2 | −0.0401 |
| cg26320504 | 7 | 157809385 | PTPRN2 | −0.0392 |
| cg24072927 | 7 | 157809451 | PTPRN2 | −0.0716 |
| cg15948324 | 7 | 157809500 | PTPRN2 | −0.0843 |
| cg00239915 | 7 | 157809596 | PTPRN2 | −0.0532 |
| cg27200869 | 7 | 158045980 | PTPRN2 | 0.0190 |
| cg16571642 | 7 | 158045996 | PTPRN2 | 0.0310 |
| cg06715136 | 7 | 158046025 | PTPRN2 | 0.0755 |
| cg02770061 | 7 | 158046166 | PTPRN2 | 0.0773 |
| cg06400119 | 7 | 158046222 | PTPRN2 | 0.0333 |
| cg10473311 | 7 | 158046358 | PTPRN2 | 0.0113 |
| cg18407955 | 7 | 158110685 | PTPRN2 | 0.0395 |
| cg17658976 | 7 | 158111178 | PTPRN2 | −0.0233 |
| cg21608691 | 7 | 158111263 | PTPRN2 | −0.0322 |
| cg12568669 | 8 | 11666485 | FDFT1 | 0.0199 |
| cg15982002 | 8 | 11666492 | FDFT1 | 0.0236 |
| cg16672706 | 8 | 11666503 | FDFT1 | 0.0184 |
| cg07242977 | 8 | 11666540 | FDFT1 | 0.0225 |
| cg24750067 | 8 | 86089494 | E2F5 | 0.0022 |
| cg14830952 | 8 | 86089500 | E2F5 | 0.0042 |
| cg00847543 | 8 | 86089503 | E2F5 | 0.0054 |
| cg05596761 | 8 | 86089793 | E2F5 | −0.0064 |
| cg03590356 | 8 | 86089841 | E2F5 | −0.0017 |
| cg04217808 | 8 | 96085270 |  | 0.0386 |
| cg22234712 | 8 | 96085385 |  | 0.0362 |
| cg24928110 | 8 | 96085448 |  | 0.0322 |
| cg17495087 | 8 | 96085689 |  | 0.0502 |
| cg27130359 | 8 | 96085994 |  | 0.0219 |
| cg17006914 | 10 | 81392746 |  | 0.0097 |
| cg10452333 | 10 | 81444403 | LOC650623 | −0.0051 |
| cg18605976 | 10 | 81453879 | NUTM2B-AS1 | 0.0158 |
| cg09793632 | 10 | 81456550 |  | 0.0126 |
| cg03269218 | 10 | 96990700 |  | −0.0566 |
| cg15454820 | 10 | 96990858 |  | −0.0759 |
| cg19476376 | 10 | 96990921 |  | −0.0744 |
| cg04539301 | 10 | 96990923 |  | −0.0827 |
| cg11335335 | 11 | 637885 | DRD4 | 0.0486 |
| cg07212818 | 11 | 638076 | DRD4 | 0.0427 |
| cg03909863 | 11 | 638404 | DRD4 | 0.0300 |
| cg05717871 | 11 | 638507 | DRD4 | 0.0473 |
| cg09386376 | 11 | 638939 | DRD4 | 0.0352 |
| cg16313227 | 11 | 638974 | DRD4 | 0.0263 |
| cg06679296 | 11 | 1949032 | TNNT3 | 0.0101 |
| cg06503573 | 11 | 1949039 | TNNT3 | 0.0161 |

TABLE 2-continued

LOAD vs. no-LOAD differentially methylated positions

| CpG ID | Chromosome | Position | Gene Symbol(s) | Mean Beta Difference (Control-AD) |
|---|---|---|---|---|
| cg01821149 | 11 | 1949090 | TNNT3 | 0.0095 |
| cg18032502 | 11 | 1949113 | TNNT3 | 0.0164 |
| cg15652404 | 11 | 1949130 | TNNT3 | 0.0129 |
| cg13301003 | 11 | 32449254 | WT1 | 0.0190 |
| cg04096767 | 11 | 32449450 | WT1 | 0.0217 |
| cg12006284 | 11 | 32449638 | WT1 | 0.0218 |
| cg24106790 | 11 | 32449728 | WT1 | 0.0278 |
| cg12982322 | 11 | 32449821 | WT1 | 0.0182 |
| cg16501028 | 11 | 32450000 | WT1 | 0.0115 |
| cg04456238 | 11 | 32450104 | WT1 | 0.0355 |
| cg20989480 | 11 | 32451461 | WT1 | 0.0192 |
| cg08787968 | 11 | 32451777 | WT1 | 0.0222 |
| cg12781568 | 11 | 32452038 | WT1 | 0.0380 |
| cg01693350 | 11 | 32452187 | WT1 | 0.0352 |
| cg15518358 | 11 | 32452365 | WT1 | 0.0248 |
| cg07520269 | 11 | 84634188 | DLG2 | −0.0501 |
| cg02707033 | 11 | 84634228 | DLG2 | −0.0338 |
| cg17096302 | 11 | 84634314 | DLG2 | −0.0536 |
| cg19130626 | 12 | 11708829 | LINC01252 | −0.0369 |
| cg16709841 | 12 | 11708901 | LINC01252 | −0.0241 |
| cg02701505 | 12 | 11709051 | LINC01252 | −0.0650 |
| cg21747310 | 12 | 11709115 | | −0.0318 |
| cg19801883 | 12 | 11709548 | LINC01252 | −0.0115 |
| cg09596958 | 12 | 58132105 | AGAP2 | 0.0227 |
| cg17921464 | 12 | 58132114 | AGAP2 | 0.0262 |
| cg08425810 | 12 | 58132558 | AGAP2 | 0.0321 |
| cg02250171 | 12 | 75783914 | GLIPR1L2 CAPS2 | 0.0278 |
| cg02981828 | 12 | 75784144 | CAPS2 GLIPR1L2 | 0.0276 |
| cg20291222 | 12 | 75784541 | GLIPR1L2 | 0.0346 |
| cg14292619 | 12 | 75784617 | GLIPR1L2 | 0.0300 |
| cg00108944 | 12 | 75784855 | GLIPR1L2 | 0.0519 |
| cg23588049 | 12 | 75784862 | GLIPR1L2 | 0.0351 |
| cg12351126 | 12 | 75784864 | GLIPR1L2 | 0.0474 |
| cg02415057 | 12 | 75784884 | GLIPR1L2 | 0.0497 |
| cg07311024 | 12 | 75785089 | GLIPR1L2 | 0.0413 |
| cg02071292 | 12 | 75785097 | GLIPR1L2 | 0.0537 |
| cg15942481 | 12 | 75785230 | GLIPR1L2 | 0.0298 |
| cg21272279 | 12 | 75785232 | GLIPR1L2 | 0.0474 |
| cg16837338 | 12 | 122018770 | KDM2B | 0.0100 |
| cg09151742 | 12 | 122018897 | KDM2B | 0.0180 |
| cg07793808 | 12 | 122019006 | KDM2B | 0.0315 |
| cg07020001 | 12 | 122019031 | KDM2B | 0.0196 |
| cg15234492 | 12 | 122019076 | KDM2B | 0.0414 |
| cg17452615 | 12 | 122019080 | KDM2B | 0.0347 |
| cg07529210 | 12 | 122019110 | KDM2B | 0.0282 |
| cg21249371 | 12 | 122019117 | KDM2B | 0.0260 |
| cg03486832 | 12 | 122019525 | KDM2B | 0.0132 |
| cg19307673 | 12 | 122287619 | HPD | 0.0206 |
| cg21053989 | 12 | 122287774 | HPD | 0.0336 |
| cg20647285 | 12 | 122287782 | HPD | 0.0388 |
| cg07120026 | 12 | 122287892 | HPD | 0.0675 |
| cg24288706 | 12 | 122287927 | HPD | 0.0912 |
| cg15842285 | 12 | 122288010 | HPD | 0.0129 |
| cg19945931 | 12 | 133022760 | | 0.0358 |
| cg05514909 | 12 | 133022853 | | 0.0370 |
| cg14169368 | 12 | 133179968 | LRCOL1 | −0.0765 |
| cg27537570 | 12 | 133179978 | | −0.0291 |
| cg10036920 | 12 | 133180045 | | −0.0396 |
| cg26621607 | 12 | 133180238 | | −0.0348 |
| cg11560654 | 13 | 27317117 | | 0.0327 |
| cg13672871 | 13 | 27317381 | | 0.0374 |
| cg20248204 | 13 | 77461279 | KCTD12 | 0.0293 |
| cg25968569 | 13 | 77461335 | KCTD12 | 0.0374 |
| cg00931644 | 13 | 77461368 | KCTD12 | 0.0524 |
| cg13673514 | 14 | 101035818 | BEGAIN | 0.0405 |
| cg01710649 | 14 | 101036064 | BEGAIN | 0.0461 |
| cg26279372 | 14 | 101036192 | BEGAIN | 0.0304 |
| cg13521842 | 14 | 101036202 | BEGAIN | 0.0349 |
| cg07787187 | 14 | 101036254 | BEGAIN | 0.0239 |
| cg09429753 | 14 | 101036289 | BEGAIN | 0.0294 |
| cg21529382 | 15 | 52942993 | FAM214A | 0.0115 |
| cg06871560 | 15 | 52944233 | KIAA1370 | 0.0476 |
| cg17766654 | 15 | 52944269 | FAM214A | 0.0437 |
| cg07491514 | 15 | 52944329 | FAM214A | 0.0226 |
| cg06977984 | 15 | 52944386 | FAM214A | 0.0284 |

TABLE 2-continued

LOAD vs. no-LOAD differentially methylated positions

| CpG ID | Chromosome | Position | Gene Symbol(s) | Mean Beta Difference (Control-AD) |
|---|---|---|---|---|
| cg05407459 | 16 | 8619531 | TMEM114 | 0.0256 |
| cg16495975 | 16 | 8619855 | TMEM114 | 0.0352 |
| cg04066637 | 16 | 8619943 | TMEM114 | 0.0369 |
| cg22669995 | 16 | 8620128 | TMEM114 | 0.0314 |
| cg07692489 | 16 | 8960972 | CARHSP1 | 0.0557 |
| cg21306072 | 16 | 8961250 | CARHSP1 | 0.0314 |
| cg20544307 | 16 | 8961293 | CARHSP1 | 0.0316 |
| cg00040278 | 16 | 8961318 | CARHSP1 | 0.0245 |
| cg09760217 | 16 | 8961382 | CARHSP1 | 0.0206 |
| cg03848856 | 16 | 69966641 | MIR140 WWP2 | −0.0040 |
| cg01735503 | 16 | 69966815 | MIR140 WWP2 | −0.0030 |
| cg03549146 | 16 | 69966902 | WWP2 MIR140 | 0.0009 |
| cg00158530 | 16 | 69966973 | MIR140 WWP2 | −0.0021 |
| cg08209934 | 16 | 69966975 | WWP2 MIR140 | −0.0001 |
| cg04703221 | 16 | 69967063 | WWP2 MIR140 | 0.0149 |
| cg00657810 | 16 | 69967212 | WWP2 | −0.0109 |
| cg00597076 | 17 | 1395880 | MYO1C | 0.0234 |
| cg20703671 | 17 | 1396001 | MYO1C | 0.0137 |
| cg09269848 | 17 | 1396074 | MYO1C | 0.0254 |
| cg22795769 | 17 | 1396123 | MYO1C | 0.0239 |
| cg06721232 | 17 | 7253308 | ACAP1 | 0.0167 |
| cg25900902 | 17 | 7253340 | ACAP1 | 0.0084 |
| cg07925670 | 17 | 7253489 | ACAP1 | 0.0151 |
| cg20217592 | 17 | 7253521 | ACAP1 | 0.0145 |
| cg15713546 | 17 | 7253539 | ACAP1 | 0.0198 |
| cg02448825 | 17 | 7253585 | ACAP1 | 0.0127 |
| cg02676175 | 17 | 7253720 | KCTD11 ACAP1 | 0.0285 |
| cg07148458 | 17 | 7254301 | KCTD11 ACAP1 | 0.0175 |
| cg07520074 | 17 | 7254443 | ACAP1 KCTD11 | 0.0161 |
| cg03666441 | 17 | 7254671 | ACAP1 KCTD11 | 0.0376 |
| cg07639694 | 17 | 7254909 | KCTD11 | 0.0203 |
| cg12418947 | 17 | 7255037 | KCTD11 | 0.0100 |
| cg03407547 | 17 | 7255461 | KCTD11 | −0.0037 |
| cg13855261 | 17 | 14206572 | HS3ST3B1 MGC12916 | 0.0074 |
| cg09570958 | 17 | 14206774 | MGC12916 HS3ST3B1 | 0.0216 |
| cg20152539 | 17 | 14206871 | HS3ST3B1 MGC12916 | 0.0306 |
| cg06005844 | 17 | 14206874 | MGC12916 HS3ST3B1 | 0.0253 |
| cg26418770 | 17 | 14206886 | MGC12916 HS3ST3B1 | 0.0222 |
| cg26572811 | 17 | 14206901 | MGC12916 HS3ST3B1 | 0.0229 |
| cg14016875 | 17 | 14206981 | HS3ST3B1 MGC12916 | 0.0217 |
| cg25647784 | 17 | 40934907 | WNK4 | 0.0486 |
| cg03294458 | 17 | 40935998 | WNK4 | 0.0152 |
| cg05614735 | 17 | 40936078 | WNK4 | 0.0049 |
| cg18963509 | 17 | 40936150 | WNK4 | 0.0289 |
| cg05886546 | 17 | 40936498 | WNK4 | 0.0212 |
| cg02441618 | 17 | 40936570 | WNK4 | 0.0040 |
| cg16265599 | 17 | 40936658 | WNK4 | 0.0092 |
| cg16695758 | 17 | 40936767 | WNK4 | 0.0108 |
| cg20653128 | 17 | 40936820 | WNK4 | 0.0365 |
| cg26066951 | 17 | 76713222 | CYTH1 | 0.0029 |
| cg23725139 | 17 | 76713283 | CYTH1 | 0.0260 |
| cg12871285 | 17 | 76713379 | CYTH1 | 0.0221 |
| cg10000837 | 17 | 76713517 | CYTH1 | 0.0297 |
| cg00774077 | 17 | 76713805 | CYTH1 | 0.0373 |
| cg05668703 | 17 | 79380493 | BAHCC1 | −0.0541 |
| cg14170999 | 17 | 79380515 | BAHCC1 | −0.0619 |
| cg19045002 | 17 | 79380585 | BAHCC1 | −0.0565 |
| cg05272827 | 17 | 79380706 | BAHCC1 | −0.0234 |
| cg14316944 | 17 | 79485529 |  | 0.0159 |
| cg24718197 | 17 | 79485709 |  | 0.0335 |
| cg17054691 | 17 | 79813439 | P4HB | 0.0175 |
| cg14492337 | 17 | 79813507 | P4HB | 0.0178 |
| cg19420720 | 17 | 79816504 | P4HB | 0.0233 |
| cg11969813 | 17 | 79816559 | P4HB | 0.0310 |
| cg08462274 | 17 | 79817079 | P4HB | 0.0170 |
| cg27334635 | 17 | 79817119 | P4HB | 0.0179 |
| cg19643276 | 17 | 79817123 | P4HB | 0.0208 |
| cg02796939 | 17 | 80545125 | FOXK2 | 0.0184 |
| cg18128058 | 17 | 80545175 | FOXK2 | 0.0261 |
| cg22582875 | 17 | 80545272 | FOXK2 | 0.0327 |
| cg14173033 | 17 | 80545310 | FOXK2 | 0.0570 |
| cg21786191 | 18 | 72916012 | ZADH2 | 0.0447 |
| cg21330207 | 18 | 72916311 | ZADH2 | 0.0540 |
| cg11568697 | 18 | 72916393 | ZADH2 | 0.0472 |
| cg02750262 | 18 | 72916776 | ZADH2 | 0.0563 |

TABLE 2-continued

LOAD vs. no-LOAD differentially methylated positions

| CpG ID | Chromosome | Position | Gene Symbol(s) | Mean Beta Difference (Control-AD) |
|---|---|---|---|---|
| cg18449964 | 18 | 72917101 | ZADH2 | 0.0706 |
| cg03972071 | 18 | 72917163 | ZADH2 | 0.0716 |
| cg07889413 | 18 | 72917369 | ZADH2 | 0.0376 |
| cg22088248 | 18 | 72917387 | ZADH2 | 0.0193 |
| cg20631204 | 19 | 9785805 | ZNF562 | 0.0098 |
| cg14073063 | 19 | 9785906 | ZNF562 | 0.0189 |
| cg17704570 | 19 | 9786027 | ZNF562 | 0.0171 |
| cg22391421 | 19 | 9786029 | ZNF562 | 0.0146 |
| cg20154743 | 19 | 9786077 | ZNF562 | 0.0111 |
| cg17691880 | 19 | 9786115 | ZNF562 | 0.0179 |
| cg16864207 | 19 | 9786131 | ZNF562 | 0.0109 |
| cg22910295 | 19 | 10403862 | ICAM5 | 0.0342 |
| cg10604476 | 19 | 10403908 | ICAM5 | 0.0524 |
| cg21994045 | 19 | 10403936 | ICAM5 | 0.0357 |
| cg03650189 | 19 | 10405083 | ICAM5 | 0.0303 |
| cg09367967 | 19 | 13050586 | CALR | 0.0244 |
| cg11341610 | 19 | 13050931 | CALR | 0.0200 |
| cg19867991 | 19 | 13051573 | CALR | 0.0260 |
| cg14000467 | 19 | 13053719 | CALR | 0.0332 |
| cg04334723 | 19 | 13054427 | CALR | 0.0303 |
| cg25605731 | 19 | 13054434 | CALR | 0.0490 |
| cg13466180 | 19 | 13054470 | CALR | 0.0295 |
| cg22625098 | 19 | 13054718 | CALR | 0.0238 |
| cg23260573 | 19 | 13055829 | RAD23A | 0.0015 |
| cg07418159 | 19 | 13056052 | RAD23A | 0.0015 |
| cg12847371 | 19 | 13056058 | RAD23A | 0.0013 |
| cg23250700 | 19 | 13056068 | RAD23A | 0.0092 |
| cg22984992 | 19 | 13056423 | RAD23A | 0.0139 |
| cg15207422 | 19 | 19280969 | MEF2B LOC729991-MEF2B | 0.0190 |
| cg26504305 | 19 | 19281019 | MEF2B LOC729991-MEF2B | 0.0112 |
| cg19540702 | 19 | 19281175 | MEF2B LOC729991-MEF2B | 0.0087 |
| cg12558012 | 19 | 19281197 | LOC729991-MEF2B MEF2B LOC729991-MEF2B | 0.0066 |
| cg15174905 | 19 | 19281255 | MEF2B | 0.0097 |
| cg17831002 | 19 | 41882232 | TMEM91 | 0.0222 |
| cg12946214 | 19 | 41882234 | TMEM91 | 0.0145 |
| cg12037898 | 19 | 41882253 | TMEM91 | 0.0109 |
| cg08676425 | 19 | 41882327 | TMEM91 | 0.0227 |
| cg09822745 | 19 | 41882331 | TMEM91 | 0.0151 |
| cg16150105 | 19 | 41882368 | TMEM91 | 0.0273 |
| cg01190023 | 19 | 41882490 | TMEM91 | 0.0271 |
| cg08136809 | 19 | 41882642 | TMEM91 | 0.0327 |
| cg25008217 | 19 | 41882654 | TMEM91 | 0.0343 |
| cg20724680 | 19 | 49000743 | LMTK3 | 0.0405 |
| cg02784823 | 19 | 49000897 | LMTK3 | 0.0311 |
| cg26280727 | 19 | 49000998 | LMTK3 | 0.0223 |
| cg06862049 | 19 | 49001890 | LMTK3 | 0.0090 |
| cg18955367 | 19 | 49002338 | LMTK3 | 0.0148 |
| cg19363466 | 19 | 59074265 | MZF1 LOC100131691 | 0.0207 |
| cg17735983 | 19 | 59074482 | LOC100131691 MZF1 | 0.0182 |
| cg00577109 | 19 | 59074507 | MZF1 LOC100131691 | 0.0050 |
| cg19776589 | 20 | 3052058 | OXT | 0.0134 |
| cg07747220 | 20 | 3052115 | OXT | 0.0144 |
| cg16887334 | 20 | 3052151 | OXT | 0.0019 |
| cg13285174 | 20 | 3052221 | OXT | 0.0233 |
| cg26267561 | 20 | 3052224 | OXT | 0.0235 |
| cg01644611 | 20 | 3052253 | OXT | 0.0148 |
| cg13725599 | 20 | 3052262 | OXT | 0.0147 |
| cg19592472 | 20 | 3052274 | OXT | 0.0345 |
| cg16712828 | 20 | 3193986 | ITPA | 0.0045 |
| cg10070314 | 20 | 3198855 | ITPA | −0.0082 |
| cg12006119 | 20 | 3199158 | ITPA | 0.0226 |
| cg08715226 | 20 | 62327732 | TNFRSF6B | 0.0162 |
| cg23773946 | 20 | 62327968 | TNFRSF6B | 0.0545 |
| cg14697761 | 20 | 62328014 | TNFRSF6B RTEL1-TNFRSF6B | 0.0717 |
| cg07620230 | 20 | 62328084 | TNFRSF6B | 0.0507 |
| cg24354818 | 20 | 62328094 | TNFRSF6B | 0.0472 |
| cg04236639 | 21 | 34402565 |  | 0.0111 |
| cg02139827 | 21 | 34404457 |  | 0.0240 |
| cg14172108 | 21 | 34405553 |  | 0.0415 |

TABLE 2-continued

LOAD vs. no-LOAD differentially methylated positions

| CpG ID | Chromosome | Position | Gene Symbol(s) | Mean Beta Difference (Control-AD) |
|---|---|---|---|---|
| cg00274965 | 21 | 34405681 | | 0.0713 |
| cg10915739 | 21 | 34405733 | | 0.0529 |
| cg04836472 | 21 | 34405997 | | 0.0365 |
| cg08752726 | 21 | 36254259 | RUNX1 | 0.0139 |
| cg01265860 | 21 | 36256316 | RUNX1 | 0.0118 |
| cg01664727 | 21 | 36258423 | RUNX1 | −0.0326 |
| cg03142697 | 21 | 36258497 | RUNX1 | −0.0336 |
| cg26974661 | 21 | 36258596 | RUNX1 | −0.0330 |
| cg02869559 | 21 | 36259067 | RUNX1 | −0.0279 |
| cg20418711 | 21 | 36259179 | RUNX1 | −0.0221 |
| cg12477880 | 21 | 36259241 | RUNX1 | −0.0282 |
| cg00994804 | 21 | 36259383 | RUNX1 | −0.0196 |
| cg14937633 | 21 | 36259397 | RUNX1 | −0.0241 |
| cg06758350 | 21 | 36259460 | RUNX1 | −0.0269 |
| cg09889857 | 21 | 36259618 | RUNX1 | −0.0357 |
| cg12083928 | 21 | 36259623 | RUNX1 | −0.0315 |
| cg07511671 | 21 | 36259694 | RUNX1 | −0.0179 |
| cg01725383 | 21 | 36259797 | RUNX1 | −0.0246 |
| cg10351617 | 21 | 47580738 | | −0.0176 |
| cg05200811 | 21 | 47581042 | | −0.0880 |
| cg11766577 | 21 | 47581405 | C21orf56 | −0.0838 |
| cg13126279 | 21 | 47581558 | C21orf56 | −0.0765 |
| cg14789911 | 21 | 47582049 | C21orf56 | −0.0509 |
| cg07747299 | 21 | 47604052 | C21orf56 | 0.0762 |
| cg08742575 | 21 | 47604166 | C21orf56 | 0.0732 |
| cg12016809 | 21 | 47604291 | C21orf56 | 0.0777 |
| cg05896524 | 21 | 47604654 | C21orf56 | 0.1153 |
| cg05672835 | 21 | 47604833 | SPATC1L | 0.0390 |
| cg13704590 | 21 | 47604898 | SPATC1L | 0.0484 |
| cg13012494 | 21 | 47604986 | C21orf56 | 0.0900 |
| cg13732083 | 21 | 47605072 | C21orf56 | 0.0955 |
| cg10296238 | 21 | 47605174 | C21orf56 | 0.1172 |
| cg26721908 | 21 | 47610096 | LSS | −0.0166 |

We claim:

1. A method for measuring the methylation level of one or more differentially methylated positions (DMPs) in B3GALT4 and/or ZADH2 comprising:
   a) extracting genomic DNA from a blood sample of a human individual suspected of having or having Alzheimer's disease;
   b) treating the extracted genomic DNA with bisulfite;
   c) amplifying the bisulfite-treated genomic DNA with primers comprising a pair of primers specific for B3GALT4 and a pair of primers specific for ZADH2; and
   d) measuring the methylation level of one or more differentially methylated positions (DMPs) in B3GALT4 and/or ZADH2 by methylation-specific PCR, quantitative methylation-specific PCR, methylation sensitive DNA restriction enzyme analysis, methylation sensitive microarray analysis, methylation-sensitive pyrosequencing, bisulfite genomic sequencing PCR or whole methylome sequencing.

2. The method of claim 1, wherein one or more of said one or more differentially methylated positions (DMPs) in B3GALT4 and/or ZADH2 is differentially methylated between a human individual with Alzheimer's disease and a human individual without Alzheimer's disease.

3. The method of claim 1, wherein said one or more differentially methylated positions (DMPs) in B3GALT4 and/or ZADH2 comprises three or more DMPs.

4. The method of claim 1, wherein said measuring the methylation level of one or more differentially methylated positions (DMPs) in B3GALT4 and/or ZADH2 comprises a primer extension assay, a structure specific cleavage assay, a 5'nuclease cleavage assay, an invasive cleavage assay or a ligation assay.

* * * * *